United States Patent
Chinn et al.

(10) Patent No.: US 9,611,975 B2
(45) Date of Patent: Apr. 4, 2017

(54) EQUIPMENT MOUNTING SYSTEM

(71) Applicant: FERNO-WASHINGTON, INC., Wilmington, OH (US)

(72) Inventors: Robert C. Chinn, Wilmington, OH (US); Timothy Paul Schroeder, Mason, OH (US); James C. West, III, Midland, OH (US); Peter Smolan, Trencin (SL); Michal Vacula, Zvolen (SL); Ladislav Turek, Trencin (SL)

(73) Assignee: Ferno-Washington, Inc., Wilmington, OH (US)

( * ) Notice: Subject to any disclaimer, the term of this patent is extended or adjusted under 35 U.S.C. 154(b) by 0 days.

(21) Appl. No.: 14/766,255

(22) PCT Filed: Feb. 11, 2014

(86) PCT No.: PCT/US2014/015898
§ 371 (c)(1),
(2) Date: Aug. 6, 2015

(87) PCT Pub. No.: WO2014/124471
PCT Pub. Date: Aug. 14, 2014

(65) Prior Publication Data
US 2016/0031382 A1 Feb. 4, 2016

Related U.S. Application Data

(60) Provisional application No. 61/763,045, filed on Feb. 11, 2013.

(51) Int. Cl.
*F16M 11/04* (2006.01)
*F16M 13/02* (2006.01)
(Continued)

(52) U.S. Cl.
CPC .......... *F16M 11/041* (2013.01); *A61B 90/50* (2016.02); *B60P 7/0815* (2013.01); *B60R 11/00* (2013.01);
(Continued)

(58) Field of Classification Search
CPC ..... B60R 2011/0059; B60R 2011/0061; B60R 2011/0073; B60R 2011/0078;
(Continued)

(56) References Cited

U.S. PATENT DOCUMENTS

| 269,985 A | 1/1883 | Joseph |
| 619,174 A | 2/1899 | Harry, II |

(Continued)

FOREIGN PATENT DOCUMENTS

| CH | 432266 A | 3/1967 |
| DE | 2000967 | 1/1970 |

(Continued)

OTHER PUBLICATIONS

Examination Report dated Feb. 5, 2016 pertaining to European Patent Application No. 14703501.8.
(Continued)

*Primary Examiner* — Jonathan Liu
*Assistant Examiner* — Guang H Guan
(74) *Attorney, Agent, or Firm* — Dinsmore & Shohl LLP

(57) ABSTRACT

A track mounting system including a mount with a mounting plate with a back surface and a front surface, the back surface is opposite the front surface and at least one mounting stud coupled to the back surface of the mounting plate, each mounting stud includes a stem portion that extends outwardly from the back surface and an enlarged head portion disposed at a distal end of stem portion. The mount also includes a release mechanism coupled to the front surface to release the mount from a track. The track mount- (Continued)

ing system also includes an adaptor coupled to the front surface of the mounting plate wherein the adaptor releasably couples with an equipment interface of a piece of equipment.

5 Claims, 34 Drawing Sheets

(51) Int. Cl.
| | |
|---|---|
| *B60P 7/08* | (2006.01) |
| *B60R 11/06* | (2006.01) |
| *B60R 11/00* | (2006.01) |
| *F16B 2/14* | (2006.01) |
| *A61B 90/50* | (2016.01) |
| *A61G 3/00* | (2006.01) |

(52) U.S. Cl.
CPC ............... *B60R 11/06* (2013.01); *F16B 2/14* (2013.01); *F16M 13/02* (2013.01); *A61G 3/00* (2013.01); *B60R 2011/0059* (2013.01); *B60R 2011/0078* (2013.01); *B60R 2011/0084* (2013.01)

(58) Field of Classification Search
CPC .......... B60R 2011/0084; F16M 11/041; F16M 13/02; F16M 2200/02; B60P 7/0807; B60P 7/0815; F16B 2/14; A61B 90/50
USPC ............ 248/220.22, 221.11, 221.12, 222.11, 248/222.13, 222.41, 223.31, 223.41, 248/224.51, 224.61, 224.8, 225.11, 316.2, 248/407, 346.03, 346.04, 346.06, 177.1, 248/178.1, 187.1; 224/547, 548, 554, 224/567, 571
See application file for complete search history.

(56) References Cited

U.S. PATENT DOCUMENTS

| | | | |
|---|---|---|---|
| 716,852 A | 12/1902 | Baker | |
| 1,178,360 A | 4/1916 | Tudor | |
| 1,263,918 A | 4/1918 | Miller | |
| 1,288,010 A | 12/1918 | Isaac | |
| 1,576,034 A | 3/1926 | Butt | |
| 1,702,937 A | 2/1929 | Friedemann | |
| 1,817,962 A | 8/1931 | Breuer | |
| 2,391,051 A | 12/1945 | Windsor | |
| 2,456,024 A | 12/1948 | Schofield | |
| 2,473,364 A | 6/1949 | Dickinson et al. | |
| 2,480,322 A | 8/1949 | Cozzoli | |
| 2,556,076 A | 6/1951 | Evans et al. | |
| 2,644,591 A | 7/1953 | McMahan | |
| 2,685,912 A | 8/1954 | Evans et al. | |
| 2,688,504 A | 9/1954 | Parker | |
| 3,042,221 A | 7/1962 | Rasmussen | |
| 3,204,998 A | 9/1965 | Stollenwerk | |
| 3,358,300 A | 12/1967 | Smith | |
| 3,375,936 A | 4/1968 | Kessler | |
| 3,392,848 A | 7/1968 | McConnell et al. | |
| 3,591,121 A | 7/1971 | Parris | |
| 3,605,637 A | 9/1971 | Prete | |
| 3,606,619 A | 9/1971 | Stollenwerk | |
| 3,613,900 A | 10/1971 | Chiu | |
| 3,718,886 A | 2/1973 | Hoffmeister | |
| 3,770,234 A | 11/1973 | Fovall | |
| 3,840,265 A | 10/1974 | Stirling et al. | |
| 3,846,944 A | 11/1974 | Lambert | |
| 4,114,947 A | 9/1978 | Nelson | |
| 4,170,335 A | 10/1979 | King | |
| 4,178,032 A | 12/1979 | Hone | |
| 4,210,355 A | 7/1980 | Legueu | |
| 4,230,432 A | 10/1980 | Howell | |
| 4,256,424 A | 3/1981 | Knox et al. | |
| 4,397,432 A | 8/1983 | Resetar et al. | |
| 4,423,817 A | 1/1984 | Monjo | |
| 4,425,978 A | 1/1984 | Star | |
| 4,458,864 A | 7/1984 | Colombo et al. | |
| 4,568,050 A | 2/1986 | Radoy et al. | |
| 4,576,319 A | 3/1986 | Brown | |
| 4,602,756 A | 7/1986 | Chatfield | |
| 4,763,360 A | 8/1988 | Daniels et al. | |
| 4,783,034 A | 11/1988 | Ostrander et al. | |
| 4,853,555 A | 8/1989 | Wheat | |
| 4,915,435 A | 4/1990 | Levine | |
| 4,974,377 A | 12/1990 | Dominitz et al. | |
| 5,007,608 A | 4/1991 | Carroll, Jr. | |
| 5,157,409 A | 10/1992 | Hamin | |
| 5,383,629 A | 1/1995 | Morgan et al. | |
| 5,425,520 A | 6/1995 | Masumoto | |
| 5,490,703 A | 2/1996 | Hewko | |
| 5,615,848 A | 4/1997 | Ceriani | |
| 5,732,965 A | 3/1998 | Willey | |
| 5,738,306 A | 4/1998 | Moss et al. | |
| 5,755,478 A | 5/1998 | Kamiya et al. | |
| 5,779,296 A | 7/1998 | Hewko | |
| 5,785,277 A | 7/1998 | Manning et al. | |
| 5,815,629 A | 9/1998 | Finzel et al. | |
| 5,850,891 A | 12/1998 | Olms et al. | |
| 5,988,409 A | 11/1999 | Gusdorf et al. | |
| 6,157,350 A | 12/2000 | House et al. | |
| 6,241,109 B1 | 6/2001 | Kautz et al. | |
| 6,273,366 B1 | 8/2001 | Sprenger et al. | |
| 6,585,188 B2 | 7/2003 | Alli | |
| 6,595,379 B1 | 7/2003 | Powell | |
| 6,618,018 B1 | 9/2003 | Sylvester et al. | |
| 6,746,138 B1 * | 6/2004 | Gamache | F21V 21/02 248/219.2 |
| 6,762,727 B2 | 7/2004 | Rochford et al. | |
| 6,945,414 B1 | 9/2005 | Stevens et al. | |
| 7,097,204 B2 | 8/2006 | Jessup et al. | |
| 7,328,926 B1 | 2/2008 | Myers et al. | |
| 7,502,226 B2 * | 3/2009 | Searby | F16M 11/04 361/679.41 |
| 7,507,005 B1 | 3/2009 | Mier-Langner | |
| 7,654,834 B1 | 2/2010 | Mier-Langner et al. | |
| 7,669,945 B2 | 3/2010 | Blersch et al. | |
| 7,677,400 B2 | 3/2010 | Bayazit et al. | |
| 7,946,771 B2 * | 5/2011 | Boneschanscher | F16M 11/02 248/187.1 |
| 7,984,889 B2 * | 7/2011 | Whitley | F16M 11/06 248/221.11 |
| 8,636,154 B2 | 1/2014 | Chinn | |
| 8,992,238 B2 | 3/2015 | Chinn | |
| 2003/0143052 A1 | 7/2003 | Fehrle et al. | |
| 2004/0178309 A1 | 9/2004 | Crowley et al. | |
| 2004/0253856 A1 | 12/2004 | Hoffmann | |
| 2005/0039644 A1 | 2/2005 | Sheahan et al. | |
| 2006/0243766 A1 | 11/2006 | Lan | |
| 2007/0097617 A1 | 5/2007 | Searby et al. | |
| 2008/0023976 A1 | 1/2008 | Myers et al. | |
| 2008/0302553 A1 | 12/2008 | Ross et al. | |
| 2009/0014584 A1 | 1/2009 | Rudduck et al. | |
| 2009/0014602 A1 | 1/2009 | Frost | |
| 2009/0140112 A1 | 6/2009 | Carnevali | |
| 2010/0307649 A1 | 12/2010 | Dominguez | |
| 2012/0006873 A1 | 1/2012 | Chinn | |
| 2012/0126075 A1 | 5/2012 | Chinn et al. | |
| 2013/0081233 A1 | 4/2013 | Lu | |
| 2013/0193179 A1 | 8/2013 | Davidson | |
| 2014/0015603 A1 | 1/2014 | Scott et al. | |
| 2014/0226315 A1 | 8/2014 | Nicieja et al. | |
| 2014/0227892 A1 | 8/2014 | Chinn | |

FOREIGN PATENT DOCUMENTS

| | | |
|---|---|---|
| DE | 3209091 A1 | 9/1983 |
| DE | 3209092 | 9/1983 |
| DE | 3230905 A1 | 2/1984 |
| DE | 8910460 U1 | 12/1989 |
| DE | 19716046 A1 | 10/1998 |
| DE | 202006020143 U1 | 1/2008 |
| DE | 102009039471 A1 | 3/2011 |

(56) References Cited

FOREIGN PATENT DOCUMENTS

| | | | |
|---|---|---|---|
| DE | 102010024544 A1 | 12/2011 |
| EP | 0021526 A2 | 1/1981 |
| EP | 105675 A2 | 4/1984 |
| EP | 260726 A2 | 1/1993 |
| EP | 583491 A1 | 9/1995 |
| EP | 972616 A2 | 12/2003 |
| EP | 1790521 A1 | 5/2007 |
| EP | 1863119 A1 | 12/2007 |
| EP | 2206623 A1 | 7/2010 |
| EP | 2451418 B1 | 5/2013 |
| EP | 2614804 A1 | 7/2013 |
| EP | 2614805 A1 | 7/2013 |
| FR | 1085340 | 1/1955 |
| FR | 2481110 A1 | 10/1981 |
| FR | 2647323 A1 | 11/1990 |
| FR | 2649007 A1 | 1/1991 |
| GB | 1530794 A | 11/1978 |
| GB | 2401541 A | 11/2004 |
| GB | 2452083 A | 2/2009 |
| WO | 9115178 A1 | 10/1991 |
| WO | 9927881 A1 | 6/1999 |
| WO | 0059446 A1 | 10/2000 |
| WO | 2006122351 A1 | 11/2006 |
| WO | 2011006163 A2 | 1/2011 |

OTHER PUBLICATIONS

International Search Report and Written Opinion pertaining to PCT/2014/012492 dated Apr. 3, 2014.
Extended European Search Report from EP Application No. 13163007.1 mailed Jun. 11, 2013.
Extended European Search Report from EP Application No. 13163002.2 mailed Jun. 11, 2013.
International Search Report and Written Opinion dated Nov. 3, 2011 pertaining to International Application No. PCT/US2010/041724.
International Search Report and Written Opinion dated Jun. 27, 2014 pertaining to International Application No. PCT/US2014/015898.
Office Action pertaining to Russian Application No. 2012101216 dated Jul. 29, 2014.
International Preliminary Report on Patentability pertaining to International Application No. PCT/US2010/041724 dated Jan. 19, 2012.
Exam Report pertaining to Australian Application No. 2010271194 dated Nov. 27, 2013.
Office Action pertaining to Chinese Application No. 201080038769.2 dated Jan. 24, 2014.
International Search Report and Written Opinion dated Apr. 16, 2013 pertaining to International Application No. PCT/US2013/026129.
International Preliminary Report on Patentability pertaining to International Application No. PCT/US2013/026129 dated Aug. 28, 2014.
Exam Report pertaining to Australian Application No. 2013203990 dated Aug. 18, 2014.
Preliminary Rejection pertaining to Korean Application No. 10-2012-7003477 dated Jul. 27, 2015.
Exam Report pertaining to Canadian Application No. 2767547 dated Jul. 7, 2015.
Exam Report pertaining to European Patent Application No. 13163007.1 dated Nov. 17, 2014.
Exam Report pertaining to Australian Patent Application No. 2014203593 dated Feb. 20, 2015.
Exam Report pertaining to Australian Patent Application No. 2014203595 dated Jul. 23, 2015.
International Preliminary Report on Patentability pertaining to International Application No. PCT/US2014/012492 dated Aug. 20, 2015.
International Search Report and Written Opinion dated Mar. 3, 2015 pertaining to International Application No. PCT/US2014/050288.
International Search Report and Written Opinion dated Mar. 3, 2015 pertaining to International Application No. PCT/US2014/050306.
International Search Report and Written Opinion dated Sep. 29, 2015 pertaining to International Application No. PCT/US2014/050392.
Examination Report dated Mar. 1, 2016 pertaining to European Patent Application No. 14707550.1.
Official Action dated Feb. 29, 2016 pertaining to Egyptian Patent Application No. PCT/NA/5012012.
Office Action dated Dec. 22, 2015 pertaining to Chinese Patent Application No. 201410247226.1.
Office Action dated Dec. 16, 2015 pertaining to Japanese Patent Application No. 2015-020347.
Notice of Allowance dated Jan. 20, 2016 pertaining to U.S. Appl. No. 14/633,797.

* cited by examiner

EQUIPMENT MOUNTING SYSTEM

CROSS REFERENCE TO RELATED APPLICATIONS

The present application hereby claims the benefit of provisional application 61/763,045 filed Feb. 11, 2013, which is herein incorporated by reference in its entirety.

TECHNICAL FIELD

The present specification generally relates to equipment mounting systems for mounting equipment in various configurations on a structure and, more specifically, a track mounting system for mounting equipment in vehicles.

BACKGROUND

Mounting equipment and devices are dependent on the manufacturer mounting locations for securing to third party structures. This may require individual adaptation for each piece of equipment or device to mount to specific locations which may be time consuming and labor intensive. Furthermore, if the piece of equipment or device is desired to be moved, the amount of time and effort is increased to re-mount the piece of equipment or device in a new location. A manufacturer may entertain adding quick mounting hardware to their equipment or devices for addition money paid for by the customer but the new hardware may not be compatible with other manufacturer's hardware.

The problem is compounded if the piece of equipment or device is desired to be mounted in a vehicle such as an ambulance, helicopter, airplane, military vehicle, ATV, cart, etc. The rigors that the securing fasteners must endure are increased over static applications. Furthermore, the occupants of the vehicle may require relocation of the piece of equipment or device away from a service area and without the need for tools.

Accordingly, a need exists for alternative approaches to secure and easily relocate equipment or devices throughout and around a vehicle.

SUMMARY

In one embodiment, a track mounting system may include a mount with a mounting plate with a back surface and a front surface, the back surface is opposite the front surface and at least one mounting stud coupled to the back surface of the mounting plate, each mounting stud includes a stem portion that extends outwardly from the back surface and an enlarged head portion disposed at a distal end of stem portion. The mount also includes a release mechanism coupled to the front surface to release the mount from a track. The track mounting system also includes an adaptor coupled to the front surface of the mounting plate wherein the adaptor releasably couples with an equipment interface of a piece of equipment.

In another embodiment, an intravenous (IV) bag kit includes an IV hook mechanism and a track. The IV hook mechanism includes a central shaft disposed along a central axis of the IV hook mechanism, a mount head coupled to a proximal end of the central shaft, a pressure collar slidably disposed on the central shaft biased towards the mount head by a release spring, and at least one hook pivotably coupled to the central shaft such that the hook is movable to a storage position and a use position. The track includes a backing plate with a plurality of slots, each slot substantially parallel to each other, each slot comprising a plurality of open regions and a plurality of necked down regions connecting the plurality of open regions wherein the mount head slideably couples with individual ones of the plurality of slots.

In yet another embodiment, an equipment track mount with a rail with a track side and an equipment side. The rail includes a plurality of mount studs coupled to the rail, individual ones of the plurality of mounting studs include a stem portion that extends outwardly from the track side and an enlarged head portion disposed at a distal end of respective stem portions, one or more threaded rods coupled to the equipment side. The rail also includes a locking pin disposed through the rail and extending outwardly from the track side in an extended position, a lock bias spring which biases the locking pin in the extended position, and a control knob coupled to the equipment side and operatively coupled to the locking pin and when actuated, retracts the locking pin into the mounting plate and when released, allows the lock bias spring to bias the locking pin in the extended position.

In another embodiment, a track may include a backing plate with a center slot, a first outer slot, and a second outer slot, the center slot comprises the backing plate, and the first outer slot and the second outer slot comprise a plurality of open regions and a plurality of necked down regions connecting the plurality of open regions and wherein every fourth open region is a target open region wherein the target open region has a larger diameter aperture than each open region.

In yet another embodiment. a quick mount track may include a backing plate with a center slot, a first outer slot, and a second outer slot, the first outer slot and the second outer slot comprise a plurality of diamond contour target regions that allow a round head of a t-shaped stud to engage the first outer slot and the second outer slot at an angle to the backing plate, the center slot has a plurality of locking pin apertures in the backing plate, the locking pin apertures are in horizontal alignment with the plurality of diamond contoured target regions.

A backing plate with a face surface and a back surface, the face surface is opposite of the back surface, the backing plate including a first outer slot with a plurality of open regions and a plurality of necked down regions connecting the plurality of open regions, a second outer slot with the plurality of open regions and the plurality of necked down regions connecting the plurality of open regions, and a center slot with a plurality of locking pin apertures in the backing plate, the locking pin apertures are in horizontal alignment with the plurality of open regions of the first outer slot and the second outer slot. The backing plate also includes a first trim tab along a first outer edge of the backing plate to support a first wall covering flush with the face surface of the backing plate, and a second trim tab along a second outer edge of the backing plate to support a second wall covering flush with the face surface of the backing plate. A support structure coupled to the back surface of the backing plate to provide support for the wall assembly wherein the wall assembly includes structure for supporting the first wall covering, the second wall covering, and an outer wall covering.

In another embodiment, a self-aligning mounting system may include a mounting plate and an equipment plate. The mounting plate may have a front surface and a back surface, the front surface is opposite the back surface. A first collar may be coupled to the front side and includes a bowl aperture. A capture plate coupled to the first collar and includes a keyhole slot aperture that partially covers the bowl aperture, the bowl aperture and the keyhole slot aperture define a landing area and a capture area, the landing area is defined as where the keyhole slot aperture and the bowl aperture are about the same size and the capture area is defined as where the keyhole slot aperture is smaller than the bowl aperture. A wedge release coupled to the first collar, a wedge bias spring coupled between the first collar and the wedge release to bias the wedge release in a locked position, at least one mounting stud coupled to the back surface, each mounting stud includes a stem portion that extends outwardly from the back surface and an enlarged head portion disposed at a distal end of stem portion, and a locking pin release coupled to the mounting plate. The locking pin release may include a locking pin disposed through the mounting plate and extending outwardly from the back surface in an extended position, a spring which biases the locking pin in the extended position, and at least one locking pin released operatively coupled to the locking pin and when actuated, retracts the locking pin into the mounting plate and when released, allows the spring to bias the locking pin in the extended position. The wedge interface may include a bowl including a plurality of capture guides, and a wedge coupled between the equipment plate and the bowl wherein the bowl matedly couples with the bowl aperture and the wedge slideably couples with the keyhole slot aperture, and when the wedge release is in an unlocked position, the equipment interface freely moves in relation to the adaptor when the wedge release is in the locked position, the capture plate is secured between the equipment plate and the plurality of capture guides.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

The following text sets forth a broad description of numerous different embodiments of the present disclosure. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

Figure 1:
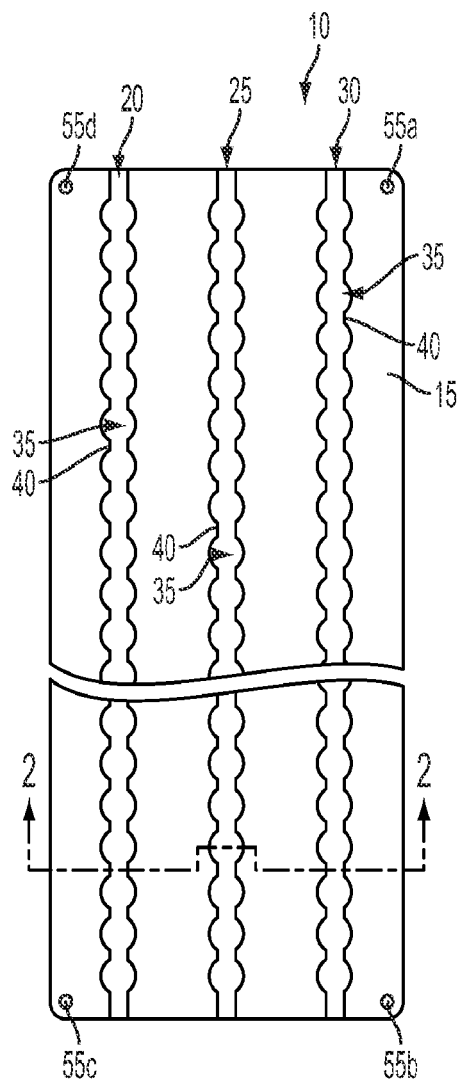
FIG. 1 depicts a perspective vie of a track according to one or more embodiments shown and described herein.
Figure 2:
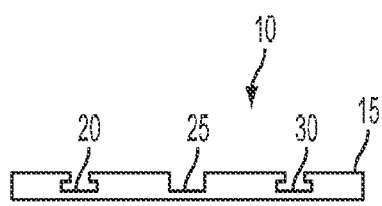
FIG. 2 depicts a cross-section of the track according to one or more embodiments shown and described herein.

Referring now to FIGS. 1 and 2, an illustrative embodiment of a track 10 for use in a track system or similar track system is illustrated. While multiple tracks can be used, only one track 10 will be described as multiple tracks of the same track system may have the same or substantially the same features. Furthermore the size, shape, and/or configuration of the track 10 can vary depending on the size of a surface for installation and the equipment to be mounted to the track 10. The track 10 includes a backing plate 15 that may have an elongated, rectangular shape (or any other suitable shape) and three slots that extend at any length along the backing plate 15. The three slots may be first outer slot 20, a center slot 25, and a second outer slot 30. The slots are best viewed in FIG. 2 as T-shaped apertures running the length of or substantially the length of the backing plate 15. The three slots are substantially parallel to each other. Each slot 20, 25 and 30 may have a series of enlarged open regions 35 that are adjacent to necked-down regions 40. In some embodiments, the enlarged open regions 35 are symmetrical such that they are spaced equidistant apart and are aligned in widthwise rows along the length of the backing plate 15. For example, two open regions 35 in the first outer slot 20 and two open regions 35 in the second outer region 30 may be spaced about 127 milli-meter (mm) (5 inches) apart. The 127 mm spacing may span any number of open regions 35 in the slot (first outer slot 20 or second outer slot 30). To illustrate the flexible spacing, every third open region may be space 127 mm apart. In yet another example, every fourth open region 35 may be spaced 127 mm apart. The 127 mm spacing is for example purposes only and any desired spacing of the open regions 25 may be used. As another example, the enlarged open regions 35 of one or more of the slots 20, 25 and 30 may not all be equidistant and/or may not be aligned in rows with the other enlarged open regions of the other slots.

The track 10 may include one or more mounting holes 55a, 55b, 55c, and 55d. The mounting holes 55a, 55b, 55c, and 55d may be used to secure the track 10 to a surface using a fastening device. Fastening devices include, but are not limited to, screws, bolts, rivets, nails, adhesive, Velcro, weld, epoxy, or any similar devices that mechanically joins or affixes two or more objects together.

Figure 3:
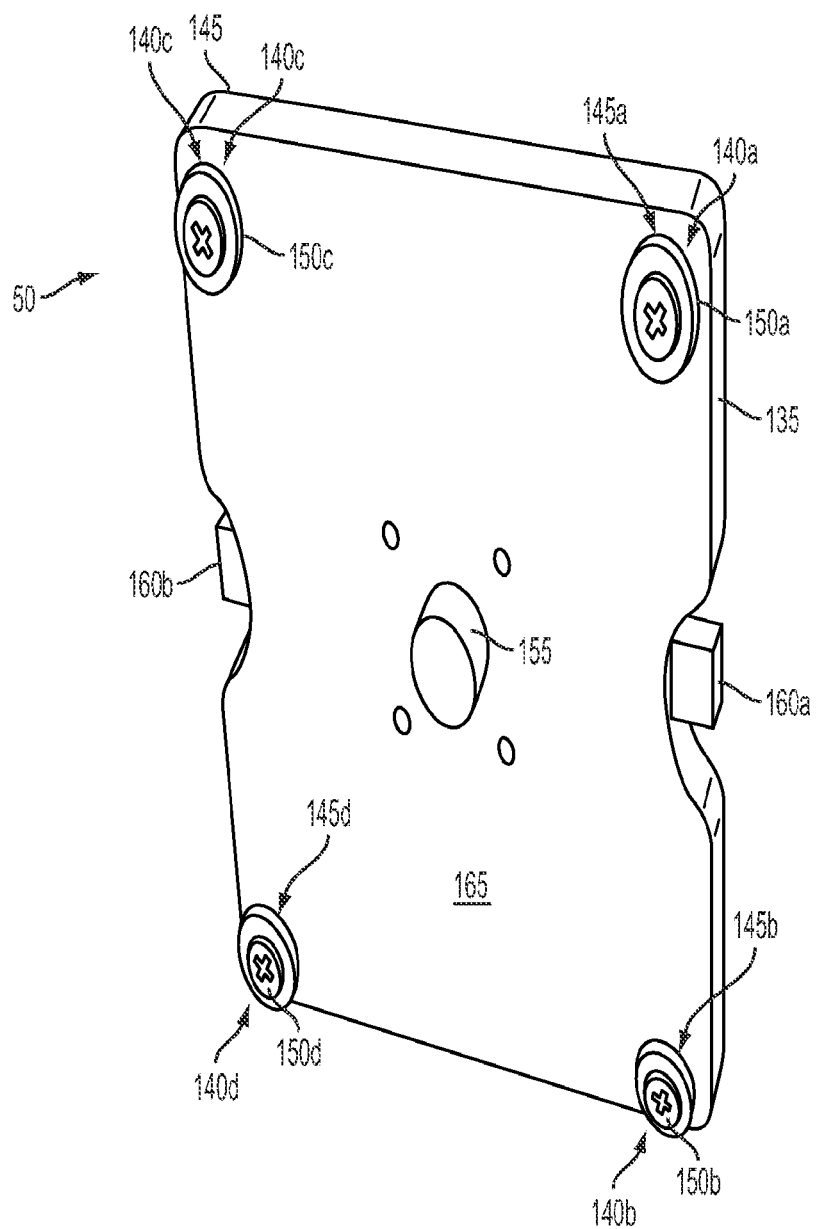
FIG. 3 depicts a perspective back view of a mount according to one or more embodiments shown and described herein.

FIG. 3 is a perspective back view of a mount 50. The mount 50 may take on many different shapes and sizes and shown in the figures and described below. The mount 50 is an interface between a piece of equipment and the track. The mount may have any number of mounting studs 140 affixed to it to support the weight of the piece of equipment or device attached to it. More mounting studs may be affixed to increase the load bearing capacity of the mount 50. The mount 50 may include apertures to reduce the weight of the mount 50.

The mount 50 has a mounting plate 135, a back surface 165, a front surface 195, and four mounting studs 140a, 140b, 140c, and 140d. The back surface 165 is on the opposite side of mount 50 from the front surface 195. The mount 50 is operable to be removably connected and/or attached to the track 10 or a fixed position plate. Each mounting stud 140a, 140b, 140c, and 140d includes a respective stem portion 145a, 145b, 145c, and 145d and a respective enlarged head portion 150a, 150b, 150c, and 150d. A locking pin 155 may be biased (e.g., by a spring, resilient material, or other biasing means) outward towards an extended lock position for engaging the track 10 of FIG. 1, and more specifically the corresponding locking pin aperture on the fixed position plate, a locking pin aperture 900 as found in FIG. 9, or the enlarged open region 35 of one of the center slot 25 of the track 10. Alternatively to the locking pin 155 engaging only the center slot 25, the locking pin 155 may be positioned on the mounting plate 135 to engage the first outer slot 20, the second outer slot 25, or both. The locking pin 155 may be retracted using either individually or in combination a right locking pin release lever 160b or a left locking pin release lever 160a which is operatively connected to a release mechanism 190 of FIG. 7. It should be understood that both locking pin releases levers 160a and/or 160b may be oriented in any direction in order to avoid obstructions with other equipment or devices and yet still allow the release of the mount 50 from the track 10. Furthermore, in some embodiments, two or more release levers may need to be actuated in order to release the mount 50 from the track 10. Such an embodiment may provide for additional security by preventing unwanted movement of the mounting plate 135 when one of the locking pin releases levers 160a or 160b is accidentally actuated. The front surface 195 may have any device and/or equipment attached to it.

Figure 9:
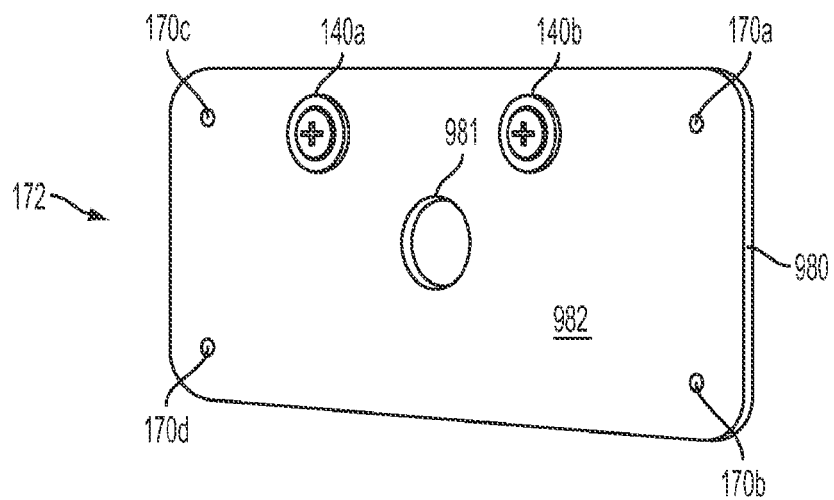
FIG. 9 depicts one example of an equipment interface according to one or more embodiments shown and described herein.

The mount 50 may be affixed to either the track 10 or the fixed position plate (not shown) using an interference fit, a friction fit, or the lock pin 155 engaging either an open region 35 or a locking pin aperture 900 of FIG. 9. For example, the mounting studs 140 may rest at the bottom of the necked down portion of the keyhole slots (not shown) of the fix position plate to attach the mount 50 to the fixed position plate. In another example, the locking pin 155 may exert a biasing force against the track 10 or the fixed position plate for the interference fit between the mount 50 and the track 10 or fixed position plate. In yet another example, the locking pin 155, as described above, may be used to immobilize the mount 50 in relation to either the track 10 or the fixed position plate by engaging either a locking pin aperture 900 or an open region 35. It should be understood that the track 10 and/or the fixed position plate are non-limiting examples of securing the mount 50.

Figure 4:
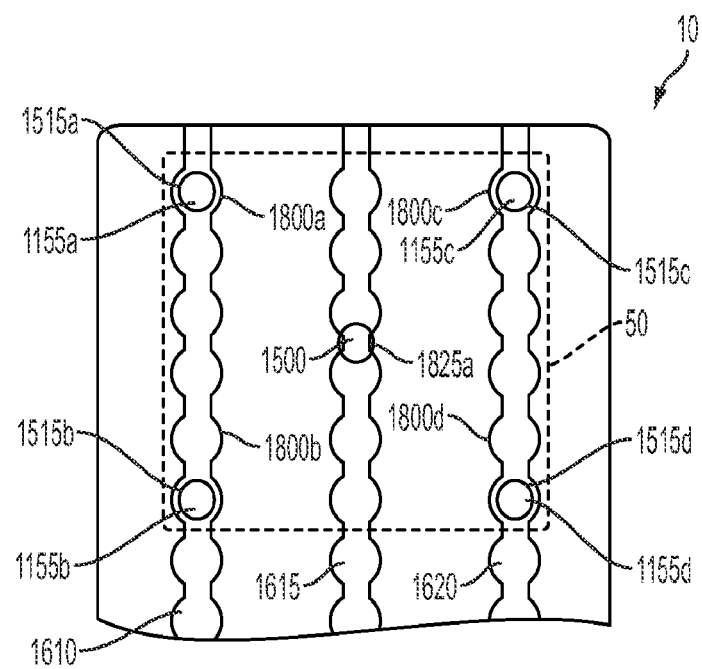
FIG. 4 depicts an in-phase configuration of the track and a mounting plate according to one or more embodiments shown and described herein.

Referring to FIG. 4, the track 10 and the mounting plate 135 illustrate an in-phase configuration that is used to lock the mounting plate 135 to the track 10. Referring to FIG. 4, when the enlarged head portions 1515a, 1515b, 1515c and 1515d of the mounting studs 1155a, 1155b, 1155c and 1155d of the mounting plate 135 are inserted within the enlarged head opening 1800a, 1800b, 1800c and 1800d of the slots 1610 and 1620, the locking pin 1500 is prevented from entering the slot 1615 due to its alignment with the necked-down portion 1825a. In some embodiments, placing the enlarged head portions 1515a, 1515b, 1515c and 1515d in the slots 1610 and 1620 causes the locking pin 1500 to retract from its outwardly biased, extended position.

Figure 5:
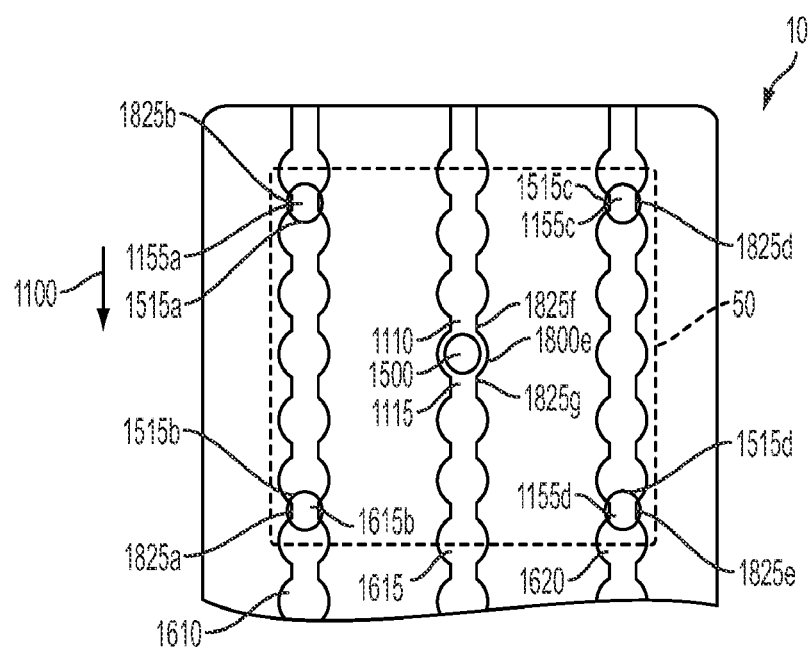
FIG. 5 depicts an out-of-phase configuration of the track and the mounting plate according to one or more embodiments shown and described herein.

Referring to FIG. 5, the track 10 and the mounting plate 135 illustrate an out-of-phase configuration. The stem portions 1510 (not shown) of the mounting studs 1155a, 1155b, 1155c and 1155d are sized to slide through the necked down portion 1825 while the enlarged head portions 1515a, 1515b, 1515c and 1515d remain in the slots 1610 and 1620. Movement of the mounting plate 135 downwardly (or upwardly) in the direction of arrow 1100 aligns the enlarged head portions 1515a, 1515b, 1515c and 1515d with necked-down regions 1825b, 1825c, 1825d and 1825e of the slots 1610 and 1620 and aligns the locking pin 1500 with the enlarged head opening 1800e of the slot 1615. The width of the locking pin 1500 may be greater than the upper passageway 1110 and the lower passageway 1115 through the necked-down regions 1825f and 1825g adjacent the enlarged head opening 1800e, which prevents further movement of the mounting plate 135 once the locking pin 1500 passes through the enlarged head opening 1800e and into the slot 1615. In embodiments where the locking pin 1500 is biased toward its extended position, the locking pin 1500 may snap into its extended position automatically once the locking pin 1500 is aligned with the enlarged head opening 1800e. An operator can retract the locking pin 1500 out of the slot 1615 by actuating any of the locking pin releases 1160/1175 described above and again move the mounting plate 135 along the track 10 to a different elevation.

While FIGS. 4 and 5 illustrate a mounting plate 135 being secured to the track 10 using four mounting studs 1155a, 1155b, 1155c, and 1155d and one locking pin 1500, it should be appreciated that any other number of studs and locking pins may alternatively be employed. Such an embodiment may allow for a secured connection under increased loads by providing more points of contact between the mounting plate 135 and the track 10. In another embodiment, the mounting plate 135 may incorporate eight studs 1155 evenly distributed about the mounting plate 135. In yet another embodiment, any other number of studs 1155 may be disposed on the mounting plate 125 that allows for a releasable connection with the track 10. The enlarged head portions 1515 are sized to be received through open regions 1625 of the slots 1610, 1615, 1620 and to be captured behind necked-down regions 1630 of the slots 1610, 1615, 1620, while the stem portions 1510 are sized to pass by the necked-down regions 1630 of the slots 610, 115, 1620.

The fixed position plate is an alternative to the track 10 of FIG. 1. A mount 50 of FIG. 3 may be removably coupled to the fixed position plate. The fixed position plate may include any suitable mounting structure or fastening device for securing it to a surface. Fastening devices include but are not limited to screws, bolts, rivets, nails, adhesive, Velcro, weld, epoxy, or any similar devices that mechanically joins or affixes two or more objects together. In this illustrative embodiment, the fixed position plate incorporates four mounting holes, to secure the fixed position plate to the surface. The fixed position plate also includes slots in the form of keyhole slots, each with an enlarged head opening and a necked-down portion. The enlarged head opening of the keyhole slots are sized and arranged to receive the enlarged head portions of the mounting studs therethrough and the necked-down portions are sized to allow the stem portions to slide therein with the enlarged head portions captured within the necked-down portions. The capture of the enlarged head portions may be accomplished by an interference fit between the mounting studs and the necked down portions of the first outer slot, or the center slot, or the second outer slot. A locking pin aperture may be provided that is sized to receive the locking pin when the locking pin is aligned with the locking pin aperture. The keyhole slots and the locking pin aperture are located as a mirror image of the mounting studs of the mount.

Figure 6:
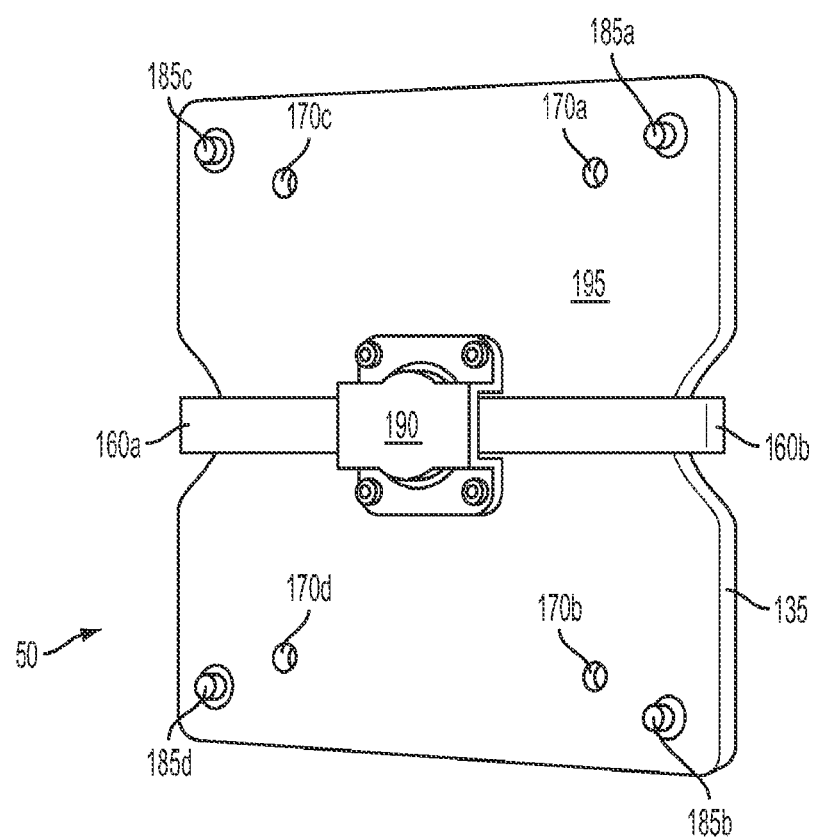
FIG. 6 depicts a perspective front view showing the front surface of another embodiment of the mount according to one or more embodiments shown and described herein.

FIG. 6 is a perspective front view showing the front surface 195 of another embodiment of the mount 50. The mounting plate 135 has equipment mounting holes 170a, 170b, 170c, and 170d used to attach the mounting plate 135 to a piece of equipment (not shown) by any of the fastening devices listed above. Although FIG. 6 only depicts four equipment mounting holes 170a, 170b, 170c, and 170d, any amount of equipment mounting holes 170, in any configuration, may be used to accommodate the equipment or device to be mounted. The stud nuts 185a, 185b, 185c, and 185d are used to secure the mounting studs 140a, 140b, 140c, and 140d to the mounting plate 135. The stud nuts 185a, 185b, 185c, and 185d may be any securing device and are not limited to a nut. The release mechanism 190 is secured to the mounting plate 135 and has gearing inside to pull in or push out the locking pin (e.g., locking pin 155 shown in FIG. 7) when one or both of the locking pin releases 160a and/or 160b are actuated. In another embodiment, the release mechanism 190 may include gearing to actuate the locking pin 155 against the bias of a spring. One example of how the release mechanism 190 works may be found in FIG. 7. The piece of equipment is secured to the front surface 195 of the mounting plate 135.

Figure 7:
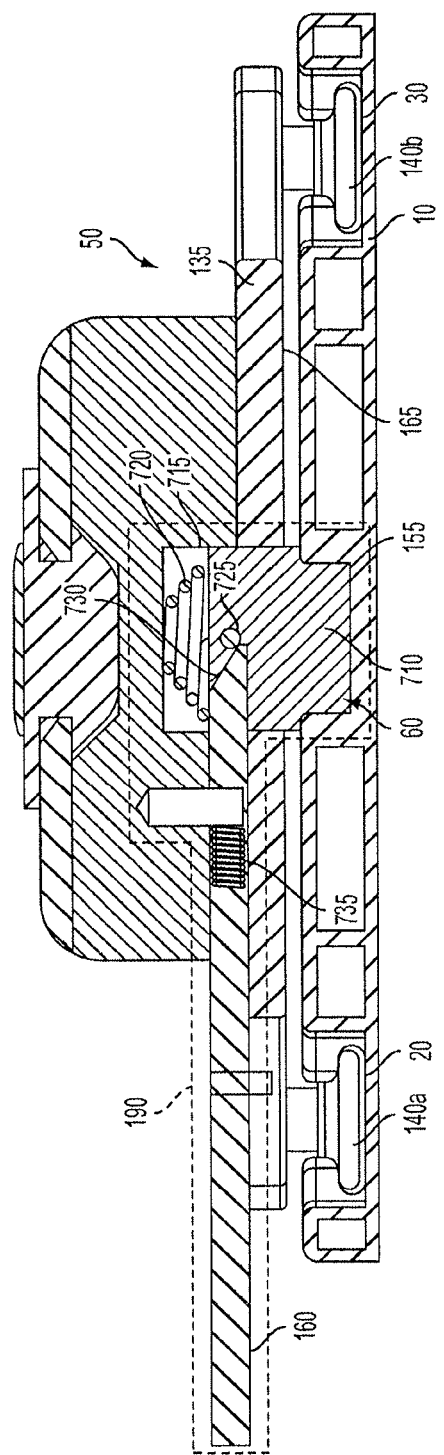
FIG. 7 depicts the inner workings of the release mechanism according to one or more embodiments shown and described herein.

FIG. 7 depicts one embodiment of the inner workings of the release mechanism 190. The locking pin 155 is shown in the extended position and extending into the locking pin aperture 60 of the track 10. The track 10 may be the embodiment shown in FIG. 28a. The release mechanism 190 may be secured in a housing 715. A spring 720 provides the biasing force to extend the locking pin 155 in the extended position. The locking pin 155 may have include a lift pin 725 that is disposed through a center of the locking pin 155. The lift pin 725 may be disposed such that to provide a mechanical neutral balance point for moving the locking pin 155 without the locking pin 155 tilting or jamming within the housing 715.

A locking pin release 160 may be used to exert a force on the locking pin 155 and against the biasing force of the spring 720 to transition the locking pin 155 from the extended position to a retracted position. The retracted position is where the distal end 710 of the locking pin 155 is flush with the back surface 165 of the mounting plate 135. The locking pin release 160 may have a ramp section 730 that, when the locking pin release 160 is transitioned towards the locking pin 155, an upward force is exerted on the lift pin 725 to retract the locking pin 155. In other words, when the locking pin release 160 is actuated, the locking pin 155 is transitioned to a retracted position. The locking pin release 160 may include a return spring 735 to provide a biasing force to return the locking pin release 160 to a locked position after actuation. The locked position is the position of the locking pin release 160 in which the mount 50 will lock into position via the locking pin 155 engaging the locking pin aperture 60.

FIG. 7 also illustrates the engagement of the mounting studs 140 (i.e. 140a and 140b) with the first outer slot 20 and the second outer slot 30.

Figure 8:
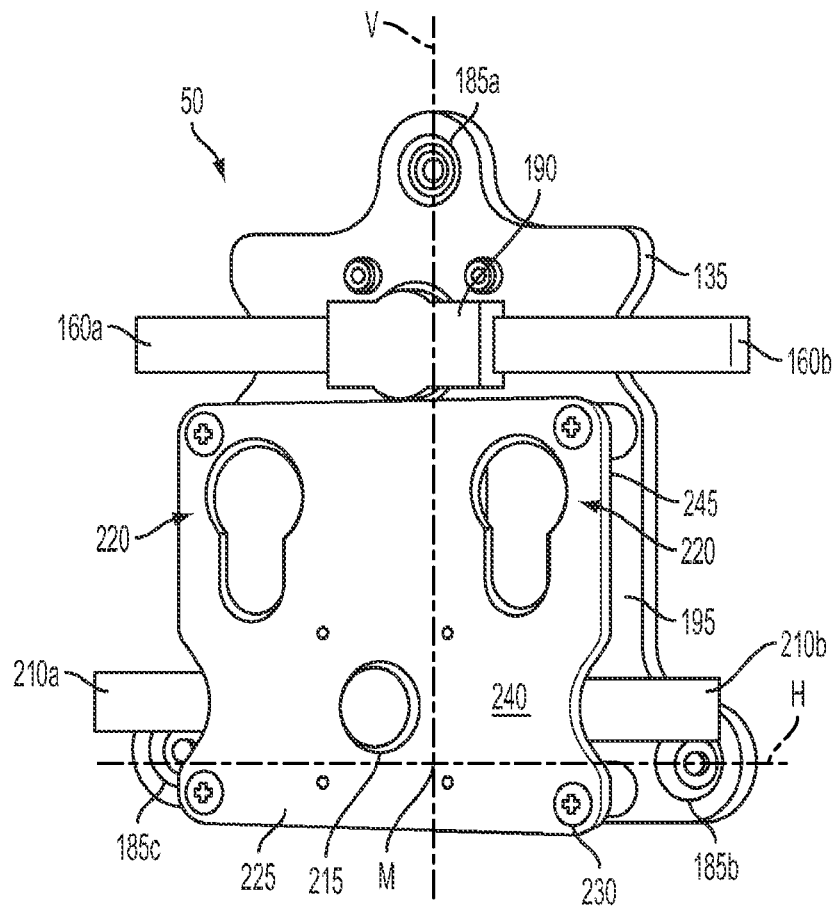
FIG. 8 depicts another embodiment of the mount according to one or more embodiments shown and described herein.

Referring generally to FIG. 8, the mount 50 may include an adaptor, described in greater detail below, coupled to the front surface 195 of the mounting plate 135 The adaptor releasably couples with an equipment interface of a piece of equipment. The adaptor allows a user to secure the mount 50 to the track without the bulk and/or weight of the piece of equipment making the securing of the mount 50 difficult. In other words, the mount 50 may be mounted directly to a piece of equipment and the engagement of the mount 50 with the track 10 may be complicated by the size, shape, weight, or other factors of the piece of equipment. The adaptor is secured to the mount 50. An equipment interface, described below, is used to couple the piece of equipment to the adaptor.

FIG. 8 depicts another embodiment of the mount 50. In this illustrative embodiment, the adaptor is a second mounting plate 225 attached to the mounting plate 135. This embodiment allows adaptors (described below), or other equipment, to be mounted to the track 10. The mounting plate 135 may have any number of mounting studs 140 required to secure the mount 50 to the track 10. If the mount 50 is required to secure a heavy load, additional mounting studs 140 may be added to increase the load capacity of the mount 50. In this embodiment, the mounting plate 135 has three stud nuts 185a, 185b, and 185c used to secure three mounting studs 140a, 140b, and 140c to the mounting plate 135. The three mounting studs 140a, 140b, and 140c may be in a triangle configuration as shown in FIG. 8. Mounting studs 185b and 185c lie along a horizontal axis H and mounting stud 185a lies along a vertical axis V. A midpoint M is the point along the horizontal axis H and is equidistant between mounting studs 185b and 185c. The vertical axis passes through the midpoint M. Mounting stud 185a is positioned to engage the open area 35 of the center slot 25 when mounting studs 185b and 185c engage an open area 35 of the second outer slot 30 and the first outer slot 20 respectively of the track 10. The locking pin associated with the locking pin release 190 may also engage the open areas 25 of the center slot 25. The stud nuts 185a, 185b and 185c may be any securing device and are not limited to a nut. The release mechanism 190 is secured to the mounting plate 135 and has gearing inside to pull in or push out the locking pin (e.g., locking pin 155 shown in FIG. 7) when one or both of the locking pin releases 160a or 160b are actuated. The second mounting plate 225 is secured to the front surface 195 of the mounting plate 135 using a fastener 230 threaded into the equipment mounting holes 170 (not shown). It should be understood that the use of the fastener 230 is a non-limiting example of a type of hardware that can be used to attach the second mounting plate 225 to the mounting plate 135, in this case a screw. Other illustrative examples of fasteners include, but are not limited to bolt/nut combinations, cotter pins, rivets, and any other fastening mechanisms. The second mounting plate 225 may include two keyholes 220 disposed therethrough for mounting equipment, devices, adaptors, and/or other items.

In one embodiment, the second mounting plate 225 may have a first surface 240 and a second surface 245, the first surface 240 is opposite the second surface 245. A second release mechanism (not shown) is coupled to the second surface 245. The second release mechanism is the same in operation and configuration as the release mechanism 190 of FIG. 7. The second release mechanism includes a second locking pin (not shown) disposed through the second mounting plate 225 and extending outwardly from the first surface 240 in an extended position. A second lock bias spring (not shown) which biases the second locking pin 215 in the extended position, and at least one second locking pin release (i.e. 210a and 210b) operatively coupled to the second locking pin 215 and when actuated, retracts the second locking pin 215 toward the second mounting plate 225 into a retracted position and when released, allows the second lock bias spring to bias the second locking pin 215 in the extended position.

FIG. 9 illustrates one example of an equipment interface 172 used to couple with the adaptor (i.e. second mounting plate 225) described above. A connect plate 980 may be used as the support structure for the equipment interface 172. Equipment mounting apertures 170a, 170b, 170c, and 170d may be used to secure a piece of equipment to the equipment interface 172. Although four mounting apertures are shown, any number of mounting apertures may be used to properly secure a piece of equipment to the equipment interface 172. The connect plate may also include a lock pin aperture 905 disposed through the connect plate and at least one mounting stud coupled to the back surface of the mounting plate, individual ones of the at least one mounting stud (i.e. 140a and 140b) that includes a stem portion that extends outwardly from a connect surface 982 and an enlarged head portion disposed at a distal end of respective stem portions. The one or more mounting studs 140a and 140b, slideably couple with individual ones of the at least one keyhole slots (i.e. 220 of FIG. 8) to secure the connect plate 980 to the second mounting plate 225. When in the locked position, the second locking pin 215 engages the lock pin aperture 905 to restrict relative movement between the connect plate 980 and second mounting plate 225.

In another embodiment of an equipment interface used with an adaptor, the connect plate 980 may include two mounting studs 140a and 140b and a locking pin aperture 981 as described above as well as a plurality of thumb screws. The thumb screws may be used to easily attach a piece of equipment (not shown) without the need for separate mounting hardware, i.e. bolts, screws, etc. The thumb screws may be of any configuration as required by the equipment to be mounted may be used.

In another embodiment of an equipment interface, the equipment interface may serve as an interface between two types of adaptors. For example, the connect plate 980 may have, on a first side, one or more mounting studs 140 and a locking pin aperture 981 and a bowl adaptor (described below) on a second side.

Another example of an equipment interface is a surface mount (not shown). The surface mount may be secured to the track 10 via the mount 50 directly or via the adaptor described above. The surface mount 250 is secured to the mount 50 via four fasteners 230. The surface mount has a handle to aid in removing the surface mount from the track when the locking pin release is actuated. The handle 265 also be used to hang an IV bag, wrap cords around or mount additional pieces of equipment to. A plurality of holes is drilled into a body of the surface mount to reduce the weight of the overall unit and organize and secure cords and other devices by routing them through the plurality of holes. In this non-limited embodiment, the plurality of holes are placed and sized where they will effectively reduce weight without weakening the structure of the body. A storage compartment is included to hold a power cord of a piece of equipment mounted to the surface mount.

In another embodiment, if the surface mount is directly mounted to the mount, the surface mount is not functioning as an equipment interface and may include an adaptor mounted to the body of the surface mount to secure a piece of equipment. The piece of equipment may incorporate the equipment interface such as a tongue and groove interface. The piece of equipment, the surface mount, and the mount would work as one unit. A mount fastener attaches the mount to the surface mount.

In yet another example of an equipment interface a Sequal Eclipse mount may be used to mount a Sequal Eclipse piece of equipment (not shown). Weight saving holes are place throughout the Sequal Eclipse mount to save weight and material. Constraint tabs and a constraint arm are used to keep the Sequal Eclipse equipment from moving and secure the Sequal Eclipse equipment to the Sequal Eclipse mount. A pair of individual tie down mounts are coupled to a tie down to capture the Sequal Eclipse equipment in the Sequal Eclipse mount. One of the tie down mounts are attached to a tie down mast that elevates the tie down mount above the Sequal Eclipse equipment. A cord holder with an access window is positioned below a deck where the Sequal Eclipse equipment rests on. The cords from the Sequal Eclipse equipment are stored in the card holder and are accessible through the access window. Sequal Eclipse fasteners are shown and used to secure the Sequal Eclipse equipment to the Sequal Eclipse mount. For example, six Sequal Eclipse fasteners may be used but they are not limited to six.

In another embodiment, if the Sequal Eclipse mount is directly mounted to the mount, the Sequal Eclipse mount is not functioning as an equipment interface. The piece of equipment, the Sequal Eclipse mount, and the mount would work as one unit. A mount fastener attaches the mount to the Sequal Eclipse mount.

In yet another example of an equipment interface an equipment holder may be used to hold portable equipment that is not mounted to the mount/track. For example, a portable ultrasound machine, thermometer, calculator, etc. may be held in place by the equipment holder. The equipment holder comprises a body with two retention tabs, two sidewalls, and a floor. The floor and the sidewalls retain the piece of equipment in the equipment holder. A hole is centered in the floor to facilitate weight savings and to allow the passage of cords or other devices through the body. The two retention tabs constrain any upper lateral movement of the piece of equipment.

In another embodiment, if the equipment holder is directly mounted to the mount, the equipment holder is not functioning as an equipment interface. The piece of equipment, the equipment holder, and the mount would work as one unit. In yet another embodiment, a mount fastener may be used to attach the equipment holder directly to the track without the need for a mount. An example of this technology may be found in FIG. 22. A pull pin is biased in a retention position by a spring and an offset frame. The pull pin has a head that may mimic the shape of the mounting stud to allow the equipment holder to be secured to track, or to a fixed position plate. The offset frame may be used to provide a pressure surface to counteract the pressure exerted by the spring on the head 54 when the head is engaged with the track. The offset frame also provides an offset from the track so the pressure is not exerted directly on the body of the equipment holder.

Focusing now on the mounting studs, another embodiment may include a single track stud. The single track stud is used to mount a piece of equipment to the track 10 of FIG. 1 mounted in a structure or vehicle. The single track stud comprises a mount head, a retaining collar, and a collar. The mount head is circular is shape with a threaded body extending from its center. The retaining collar and friction collar are rotated onto the threaded body. The collar has a collar engagement surface. The mount head has a mount head engagement surface. When the mount head is inserted into the track 10, the collar, may be rotated in a clockwise direction to enable the collar engagement surface and the mount head engagement surface to apply pressure to the track 10 to secure the single track stud from moving on the track 10.

The single track stud is a versatile stud that enables a variety of configurations of single track stud locations on the piece of equipment. The only limitation to those configurations is that the single track stud locations must align with the slots (i.e. 20, 25, 30) and open regions 35 on the track 10. When the single track stud is secured to the piece of equipment, the retaining collar is rotated counter clockwise to apply pressure against the piece of equipment to ensure the threaded body does not rotate out of the piece of equipment during use. The single track stud may include a spring to provide the biasing force needed to apply the pressure against the track 10.

Figure 10A:
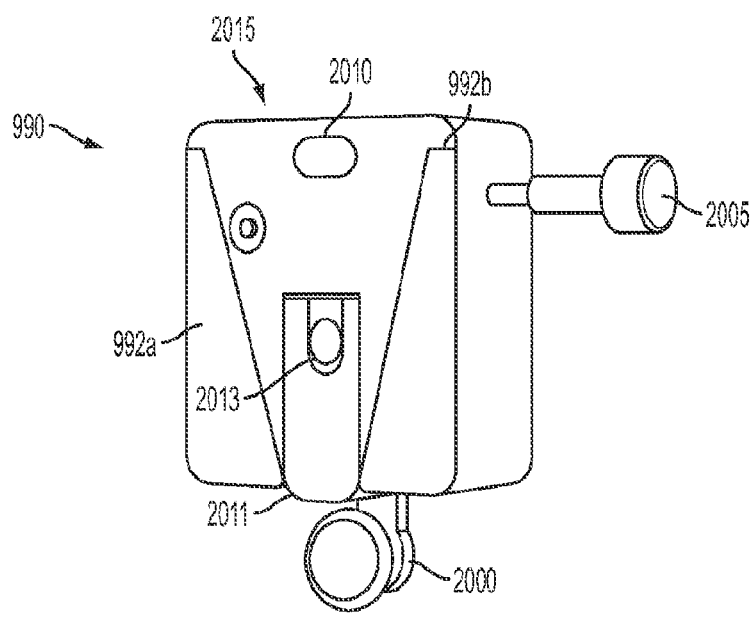
FIGS. 10A and 10B depict a universal adaptor according to one or more embodiments shown and described herein.
Figure 10B:
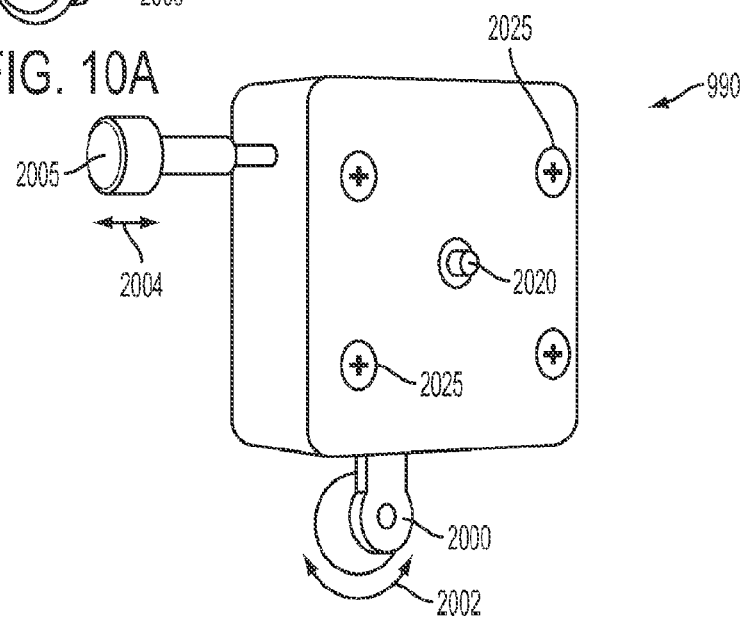

FIGS. 10A and 10B, depict another embodiment of the adaptor as a universal adaptor 990. A receiver groove 2015 may allow the universal adaptor 990 to slideable couple with a piece of equipment or other item with a tongue 2026 of FIG. 10C that corresponds to the receiver groove 2015. The receiver groove 2015 is bounded by a plurality of guides 992a and 992b. The plurality of grooves 992a and 992b matedly couple with the tongue 2026 and mimic a tongue and groove coupler. A receiver equipment lock 2010 secures the tongue 2026 to the universal adaptor 990. A receiver equipment release 2005, when actuate as shown by the arrows 2004, disable the receiver equipment lock 2010 to allow the piece of equipment or tongue 2026 to be slideably decoupled from the universal adaptor 990. A receiver locking pin 2020 may be biased (e.g., by a spring, resilient material, or other biasing means) outward towards an extended, lock position for engaging the associated track 10, and more specifically the corresponding locking pin opening 60 on the track 10. The receiver locking pin 2020 may be retracted using a receiver mount release 2000. A plurality of receiver studs 2025 may extend outwardly from one side of the universal adaptor 990. The plurality of receiver studs 2025 may operate similarly to the mounting studs 140 of FIG. 7 to secure the universal adaptor 990 to the track 10, fixed position plate 130, or similar mounting surface. The lever 2000 actuates the snubber function as described below. The snubber function is actuated along the arrows 2002.

Figure 10C:
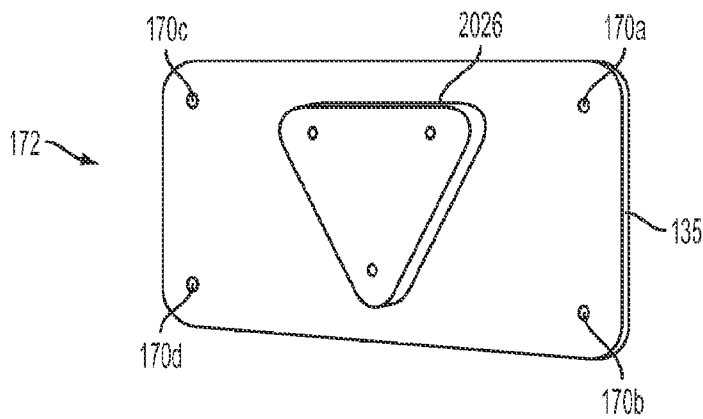
FIG. 10C depicts another embodiment of the equipment interface according to one or more embodiments shown and described herein.

FIG. 10C depicts another embodiment of the equipment interface 172. Equipment mounting apertures 170a, 170b, 170c, and 170d may be used to secure a piece of equipment to the equipment interface 172. The tongue 2026 is configured to releasably couple with the receiver groove 2015 of FIG. 10A.

Figure 11:
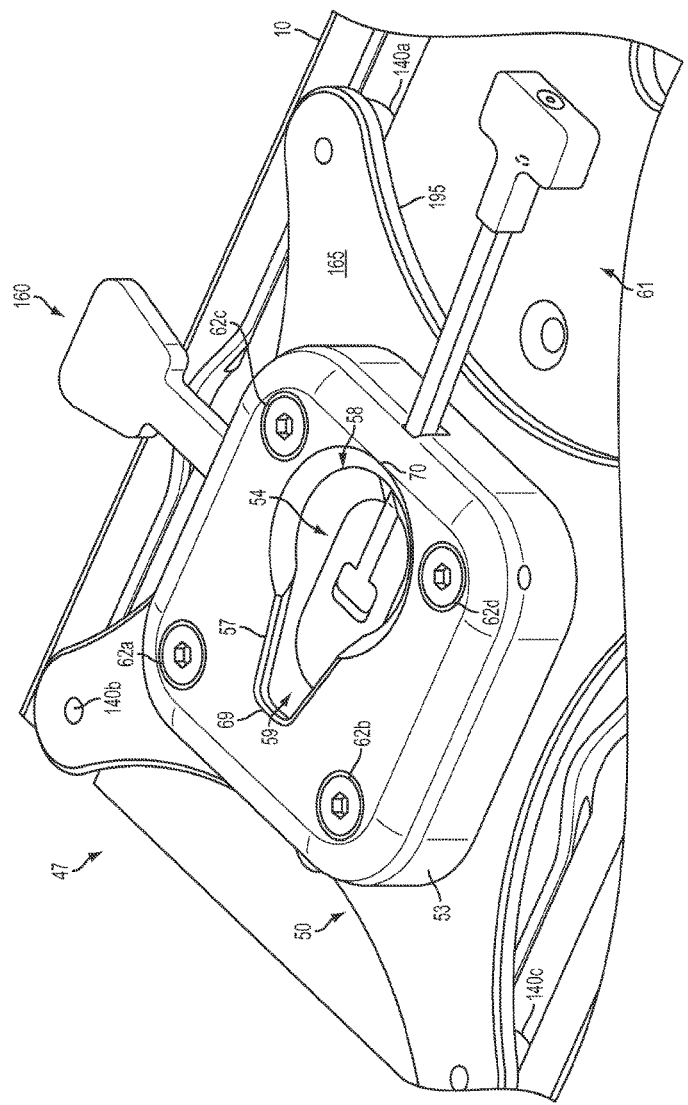
FIG. 11 depicts a wedge mount of a self-aligning mounting system according to one or more embodiments shown and described herein.

FIG. 11 depicts wedge mount 47 of a self-aligning mounting system. The wedge mount includes the mounting plate 135, the back surface 165, the front surface 195, and four mounting studs 140a, 140b, 140c, and 140d (not shown). The back surface 165 is on the opposite side of mount 50 from the front surface 195. A first collar 53 is coupled to the back surface and includes a bowl aperture 54. A capture plate 56 is coupled to the first collar 53 and includes a keyhole slot aperture 57 that partially covers the bowl aperture 54. The keyhole slot aperture 57 has a narrow end 75 and a wide end 70. The bowl aperture 53 and the keyhole slot aperture 57 define a landing area 58 and a capture area 59. The landing area 58 is defined as where the keyhole slot aperture 57 and the bowl aperture 53 are about the same size and the capture area 59 is defined as where the keyhole slot aperture 57 is smaller than the bowl aperture 53. A wedge release 61 is coupled to the first collar 53 and a wedge bias spring 102 (FIG. 13) is coupled between the first collar 53 and the wedge release 61 to bias the wedge release 61 in a locked position. At least one mounting stud (i.e. 140a, 140b, 140c, and 140d) is coupled to the front surface 195, each mounting stud includes a stem portion that extends outwardly from the back surface 168 and an enlarged head portion disposed at a distal end of stem portion. A locking pin release 160 is coupled to the mount 50 and, referring to FIG. 7, includes a locking pin 155 disposed through the mounting plate 135 and extending outwardly from the back surface 165 in an extended position. A spring 720 biases the locking pin 165 in the extended position and at least one locking pin released 160 operatively coupled to the locking pin 165 and when actuated, retracts the locking pin 165 into the mounting plate 135 in a retracted position and when released, allows the spring 720 to bias the locking pin 165 in the extended position.

Figure 12:
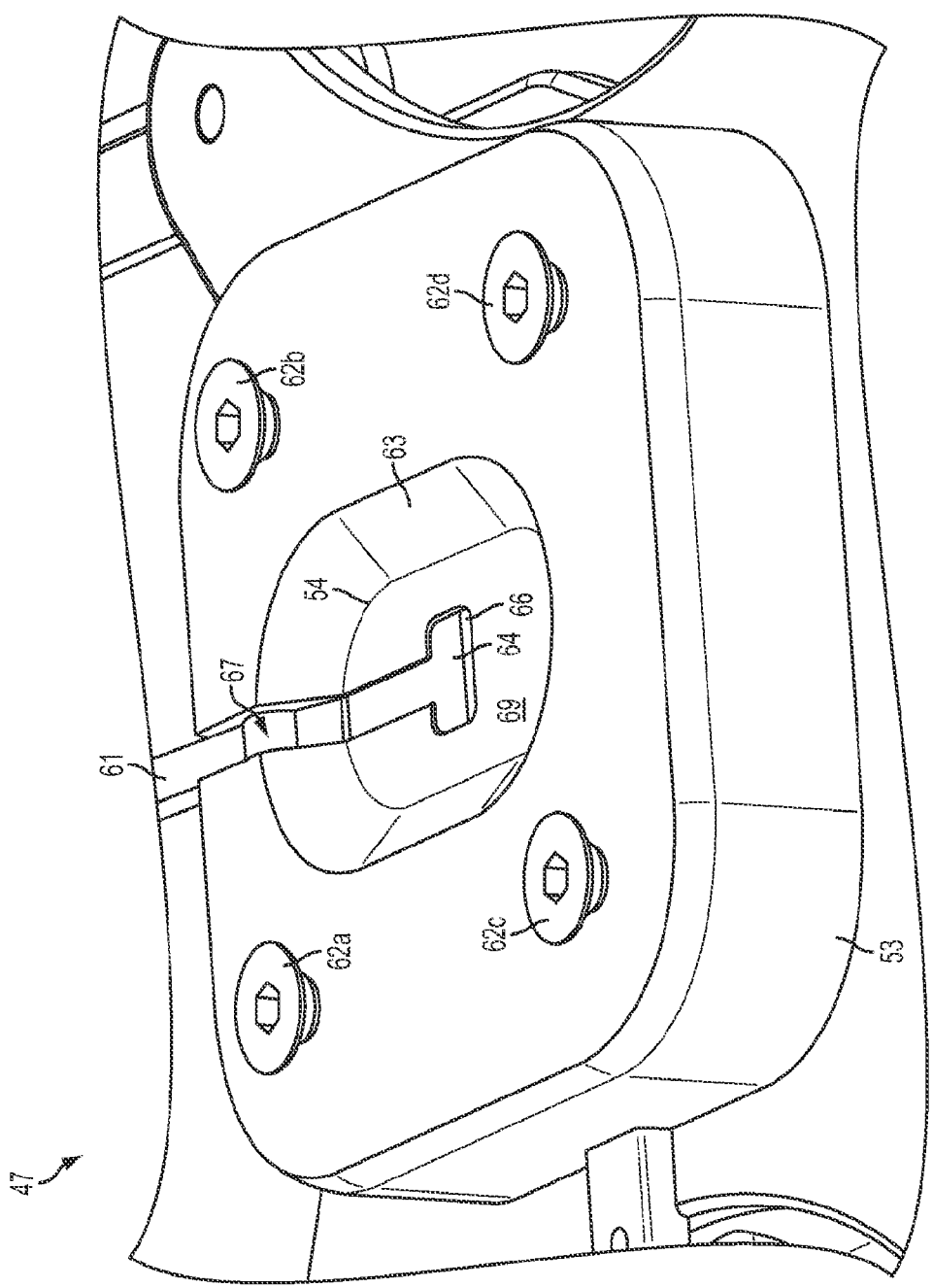
FIG. 12 depicts the first collar of the wedge mount according to one or more embodiments shown and described herein.

Referring to FIGS. 11 and 12, one or more fastening devices 62a, 62b, 62c, and 62d, may be used to secure the capture plate 56 and first collar 43 to the mounting plate 135. The fastening devices 62a, 62b, 62c, and 62d may also be used to secure the locking pin release 160 and associated parts to the mounting plate 135. Although four fastening devices 62a, 62b, 62c, and 62d are shown, it should be understood that more or less number of fastening devices may be used. The mount 50, as shown, is in a "X" shape that aids in weight reduction and also in observing the engagement of the one or more mounting studs 140 with the slots (20, 25, and 30) of the track 10. The wedge mount 47 may be mounted as an adaptor as described above instead of the structure associated with the second mounting plate 225.

FIG. 12 illustrates the first collar 53 of the wedge mount 47. The wedge release 61 has a blade 64 that used to increase the surface area of the engagement surface 66. This increase area aids in retaining a wedge interface 72 (FIG. 14) within the bowl aperture 54 and underneath the capture plate 56. The wedge release 61 pivots around a pivot point 67. Referring back to FIG. 11, the wedge release 61 has a handle 68 to aid in actuating the wedge release 61 between an unlocked position and a locked position. The bowl aperture 54 has a plurality of guide walls 63 that are used to center the wedge interface 72 when it is placed within the bowl aperture 54. The guide walls 63 surround the bowl aperture 54 and may be of any inclination to facilitate the centering of the wedge interface 72.

Figure 13:
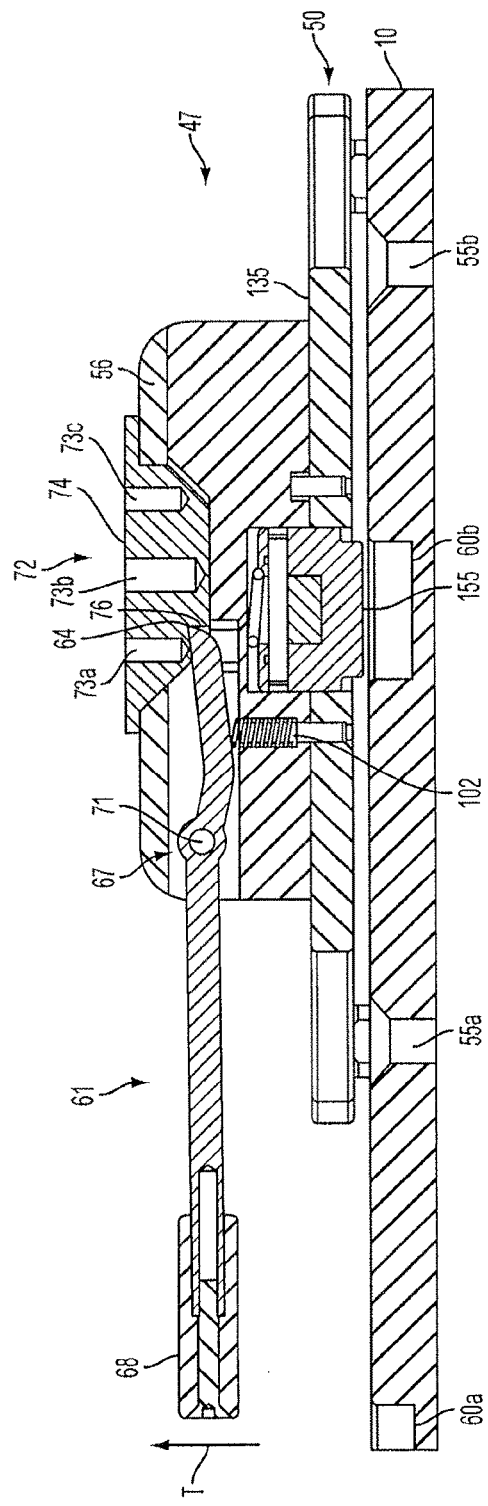
FIG. 13 depicts a cross-sectional view of the wedge mount according to one or more embodiments shown and described herein.

FIG. 13 depicts a cross-sectional view of the wedge mount 47 where the cross-section is taken right down the center of the center slot 25 of FIG. 1 of the track 10. The wedge interface 72 is shown seated in the wedge mount 47 with the wedge release 61 in the locked position. The wedge released 61 is biased into the locked position by the spring 102. In the embodiment shown, the wedge bias spring 102 is positioned in a slot within the first collar and biases the blade 64. The blade 64 engages an engagement trough 76 in an equipment plate 74 of the wedge interface 72. The pivot point 67 is shown with a pin 71 used as the fulcrum point. The handle 68 would be actuated in an upward direction along arrow T to actuate the wedge release 61 from the locked position to the unlocked position. In the unlocked position, and referring to FIG. 12, the blade is flush with a bottom surface 69 of the bowl aperture 54. Comparing FIG. 12 to FIG. 13, the capture plate 56 provides a protective cover for the pivot point 67 of the wedge release 61. Mounting holes 55a and 55b are shown in the center slot 25 of the track 10, alternating with the locking pin apertures 60a and 60b. The wedge interface 72 may have one or more fastening aperture 73a, 73b, and 73c in the equipment plate 74.

Referring to FIGS. 13 and 7, FIG. 13 is the viewed perpendicularly to FIG. 7. The locking pin 155 is shown in the retracted position in FIG. 13 whereas the locking pin 155 is shown in the extended position in FIG. 7

Figure 14:
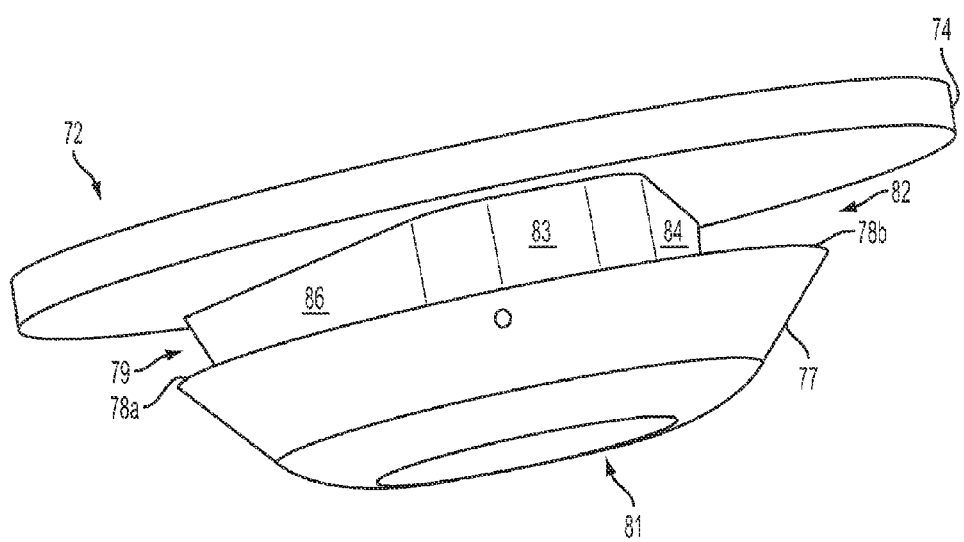
FIG. 14 depicts a front view of a wedge interface according to one or more embodiments shown and described herein.

FIG. 14 depicts a front view of the wedge interface 72. The wedge interface 72 may include the equipment plate 74, a bowl 77, a plurality of capture guides 78a and 78b, and a wedge 79. The equipment plate 74 provides the mounting point for securing the wedge interface 72 to a piece of equipment (not shown). The equipment plate 74 also provides one of two barriers to capture the keyhole slot aperture 57 of the capture plate 56 as shown in FIG. 11. The other barrier is the plurality of capture guides 78a and 78b. The capture space 82, between the equipment plate 74 and the plurality of guides 78a and 78b has a tolerance to allow the wedge interface 72 to slideably couple with the capture plate 56 and not allow a lot of undue motion between the wedge interface 72 and the capture plate 56. The wedge 79 is situated between and couples the equipment plate 74 and the plurality of capture guides 78a and 78b together. The wedge 79 has a lead-in surface 83 which is configured to engage the keyhole slot aperture 57 and aid in rotational alignment of the wedge interface 72 and the wedge mount 47. In other words, the lead-in surface 83 is configured to rotational align the wedge interface 72 and the wedge mount 47 by ensuring the lead-in surface 83 is the only part of the wedge interface 72 that may enter the capture area 59 of the keyhole slot aperture 57. The wedge 79 also includes a first incline surface 84 and a second incline surface 86. The first incline surface 84 and the second incline surface 86 are opposite each other and are coupled to the lead-in surface 83.

Figure 15:
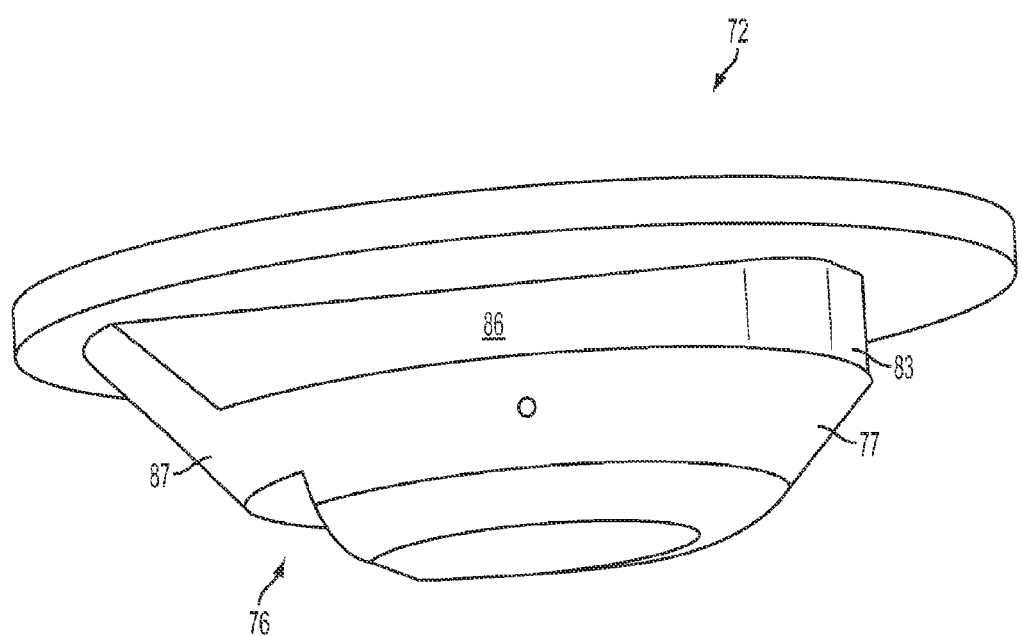
FIG. 15 depicts a side view of the wedge interface according to one or more embodiments shown and described herein.

FIG. 15 is a side view of the wedge interface 72. The capture trough 76 is shown as a notch on the bowl 77. The exit surface 87 has a slope that follows the same angle of the slope of the bowl 77. The slope allows the bowl 77 to center the wedge interface 72 in the landing area 58 as shown in FIG. 11.

A method to secure a piece of equipment to a wall may include securing a medical device (not shown) to an wedge interface 72. The wedge interface 72 may include an equipment plate 74, a bowl 77 with a plurality of capture guides 78a and 78b, and a wedge 79 coupled between the equipment plate 74 and the bowl 77. A track 10, the minitrack 12, or quick mount track 11 may be coupled to a wall (not shown) or other surface or structure. The mounting of a wedge mount 47 to the track 10 or 11 may be done by aligning one or more mount studs 140a, 140b, 140c, and 140d on the wedge mount 47 with one or more diamond contoured target regions 13 and slideably coupling the wedge mount 47 to a locked position where a locking pin 155 engages a locking pin aperture 60. The wedge mount 47 with an back surface 165 and a front surface 195. The wedge mount 47 includes a first collar 53 coupled to the front surface 195 and includes a bowl aperture 54, a capture plate 56 coupled to the first collar 53 and includes a keyhole slot aperture 57 with a wide end 70 and a narrow end 75 that partially covers the bowl aperture 54, the wide area 70 of the keyhole slot aperture 57 and corresponding bowl aperture 54 define a landing area 58 and the narrow end 75 of the keyhole slot aperture 57 and corresponding bowl aperture 54 define a capture area 59. A wedge release 61 is coupled to the first collar 53. A wedge bias spring (i.e. spring 102) is coupled between the first collar 53 and the wedge release 61 to bias the wedge release 61 in a locked position. At least one mounting stud 140a, 140b, 140c, and 140d, are coupled to the back surface 165, each mounting stud 140a, 140b, 140c, and 140d may include a stem portion that extends outwardly from the back surface 165 and an enlarged head portion disposed at a distal end of stem portion. Aligning the wedge interface 72 to the wedge mount 47 is accomplished by pressing the bowl 77 into the landing area 58 through the wide end 70 of the keyhole slot aperture 57 and into bowl aperture 54 and allowing a plurality of guide walls 63 of the bowl aperture 54 to engage a plurality of sloped sides of the bowl 77 which force the wedge interface 72 into alignment with the wedge mount 47. Coupling of the equipment plate 74 with the wedge mount 47 is accomplished by slideably moving the wedge 79 of the equipment plate 74 into the capture area 59 at the narrow end 75 of the keyhole slot aperture 57 until the capture plate 56 is secured between the equipment plate 74 and the plurality of capture guides 78. Locking the wedge interface 72 into the wedge mount 47 is accomplished by the wedge bias spring (i.e. spring 102) biasing the wedge release 61 in the locked position. Unlocking the wedge interface 72 from the wedge mount 47 is accomplished by actuating the wedge release 61 into an unlocked position and uncoupling the wedge interface 72 from the wedge mount 47 by slideably moving the wedge 79 of the wedge interface 72 out of the narrow end 75 of the keyhole slot aperture 57 until the capture plate 56 is in the wide area 70 of keyhole slot aperture 57. Removing the wedge interface 72 and hence the piece of equipment from the wedge mount 47 is accomplished by pulling the bowl 77 out of the bowl aperture 54. It is to be noted that vision of the alignment of the bowl 77 and landing area 58 is not required. The sloped surface or sides of the bowl 77 allow the wedge interface 72 to center itself and the piece of equipment in the landing area 58. The capture plate 56 also has a set of sloped surface surrounding the keyhole slot aperture 57 that further guide the bowl 77 into the landing area 58.

Figure 16A:
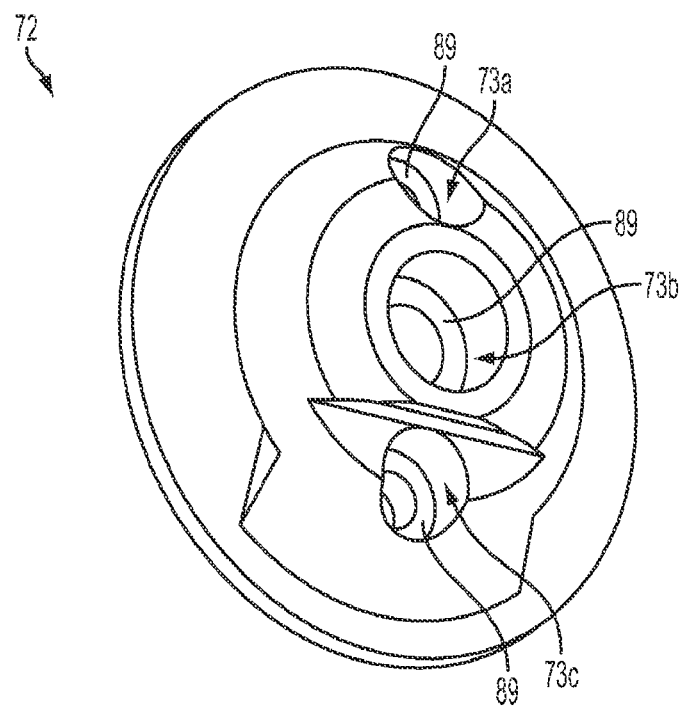
FIG. 16A depicts a perspective view of the wedge interface according to one or more embodiments shown and described herein.
Figure 16B:
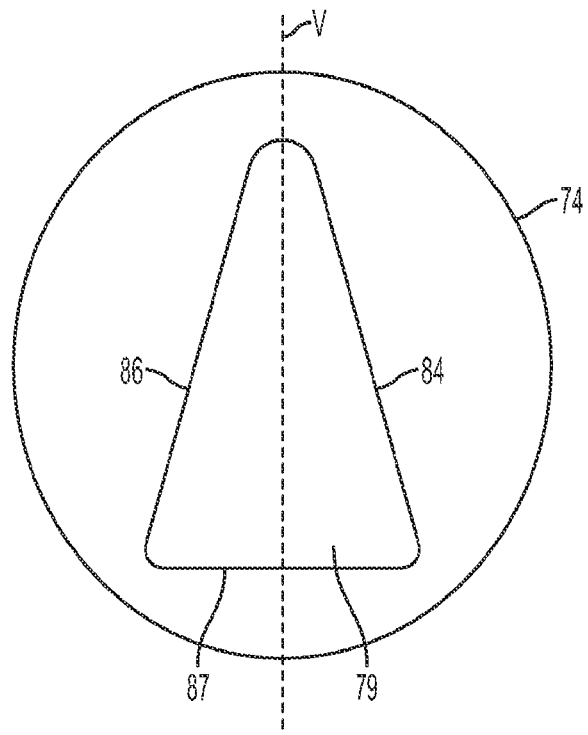
FIG. 16B depicts a bottom view of the wedge interface with a bowl removed according to one or more embodiments shown and described herein.

FIG. 16a depicts a perspective view of the wedge interface 72. The one or more fastening apertures 73a, 73b, and 73c may have a taper or ledge 89 to them to allow a fastening device, described above, to secure the wedge interface 72 to the piece of equipment. FIG. 16b depicts a bottom view of the wedge interface 72 with the bowl 77 removed. The first include surface 84 and the second incline surface 86 provide in increasing or decreasing thickness of the wedge 79 as you move along the vertical axis V. The shape of the wedge 79 may about match the shape of the keyhole slot aperture 57 in the capture area 59 as shown in FIG. 11. Therefore, as the wedge 79 is inserted into the capture area 59, either the first incline surface 84 and the second incline surface 86 will contact the keyhole slot aperture 57 first and provide a momentum to rotate the wedge interface 72 to align the wedge 79 with the narrow end 75 of the keyhole slot aperture 59. When the wedge interface 72 is seated and the wedge release 61 is in the locked position, the first incline surface 84 and the second incline surface 86 will contact both sides of the narrow end 75 of the keyhole slot aperture 57. A contact surface 81 will contact the bottom 69 of the bowl aperture 54. An exit surface 87 is wider than the lead-in surface 83 and wider than the narrow end 70 of the keyhole slot aperture 57.

Figure 17:
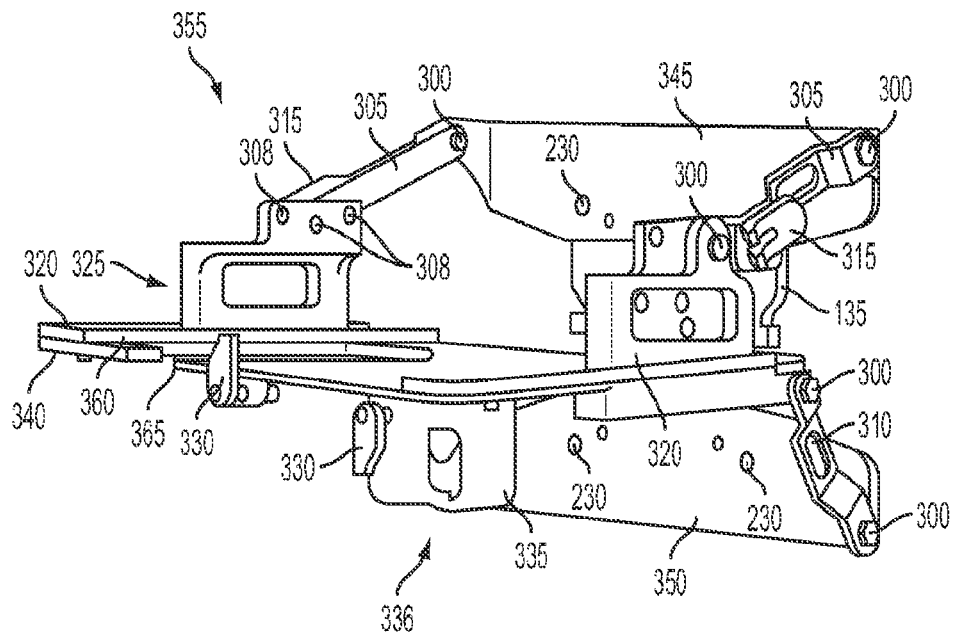
FIG. 17 depicts a folding tray in a use position according to one or more embodiments shown and described herein.
Figure 18:
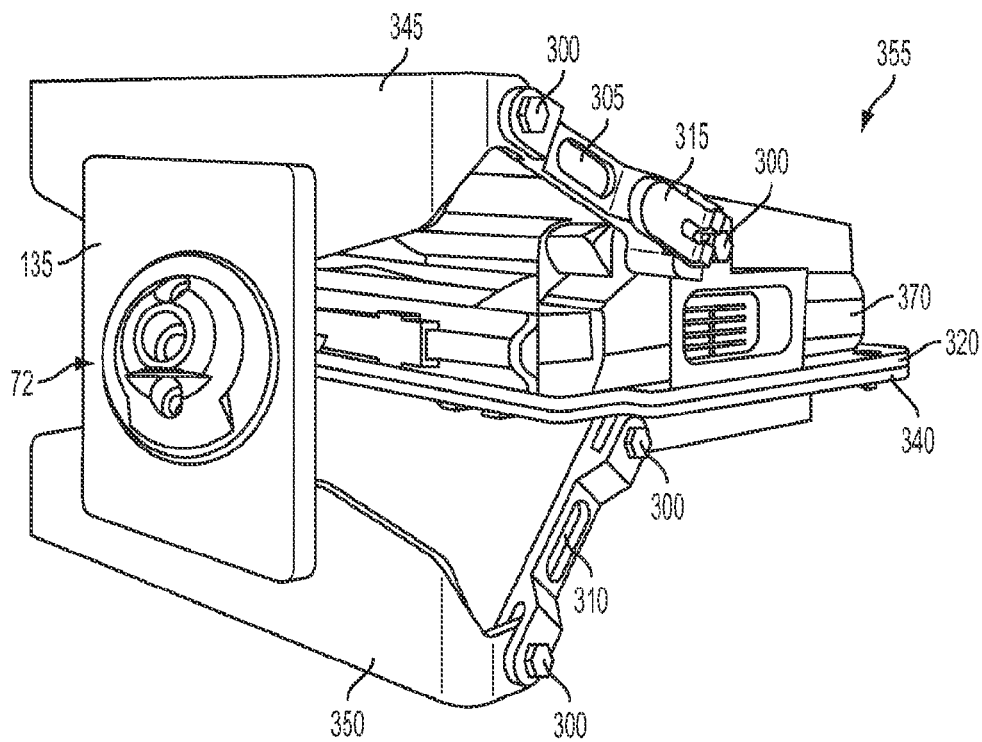
FIG. 18 depicts another perspective of the folding tray in the use position according to one or more embodiments shown and described herein.

FIGS. 17 and 18 are perspective views of a folding tray 355. The folding tray 355 incorporates a tray 340 which may be moved between a storage position, parallel to the mounting plate 135 and a use position, perpendicular to the mounting plate 135. The tray 340 may hold, secure, and/or support items or equipment such as, for example, a lap top computer. When in the use position, the tray 340 may position the equipment such that a user may operate the equipment. When in the store position, the tray 340 is positioned such that both the equipment and itself are oriented parallel with the mounting plate 135 and thus in a more compacted position.

FIGS. 17 and 18 depict the folding tray 355 in the use position. Two sets of upper arms 305 and lower arms 310 are connected to an upper support 345 and a lower support 350 via a set of hinges 300. The upper arms 305 and lower arms 310 are connected to the tray 340 via a set of hinges 300 and are used to support the tray 340 in both the storage and use positions. A left and right slot 325 are affixed to the upper portion 360 of the tray 340 and are used in conjunction with a pair of cams 330 and a pair of non-skid pads 320 to secure a piece of equipment 370. The pair of non-skid pads 320 are used to keep the piece of equipment 370 in place through a friction fit between the pair of non-skid pads 320 and the slot 325. The pair of non-skid pads 320 also have a dynamic modulus that allows for the absorption of vibrations transmitted through the folding tray 355. A set of lock tabs 315 are used to prevent the upper arms 305 and lower arms 310 from moving from the storage to the use position and vice versa. A guide element 335 is attached to a lower portion 365 of the tray 340. In this non-limited embodiment, the guide element 335 is an oblong piece with an open slot 336 to allow for the insertion of cords or other items. The upper support 345 and lower support 350 are secured to the mounting plate 135 of the mount 50 via four fasteners 230. In this non-limiting embodiment, the fasteners 230 are bolts used to secure the folding tray 355 to the mounting plate 135. The upper and lower support 345 and 350 respectfully may be adjusted to allow for different angles of the tray 340 from perpendicular to the mounting plate 135 by moving hinge 300 to a different adjustment hole 308.

The mounting plate 135 may have a variety of equipment interfaces attached as well as mounting studs and locking pin 155 as shown in FIG. 3. In FIG. 18, the wedge interface 72 is shown coupled to the mounting plate 135 for releasably coupling with a wedge mount 47 as shown in FIG. 11.

Figure 19:
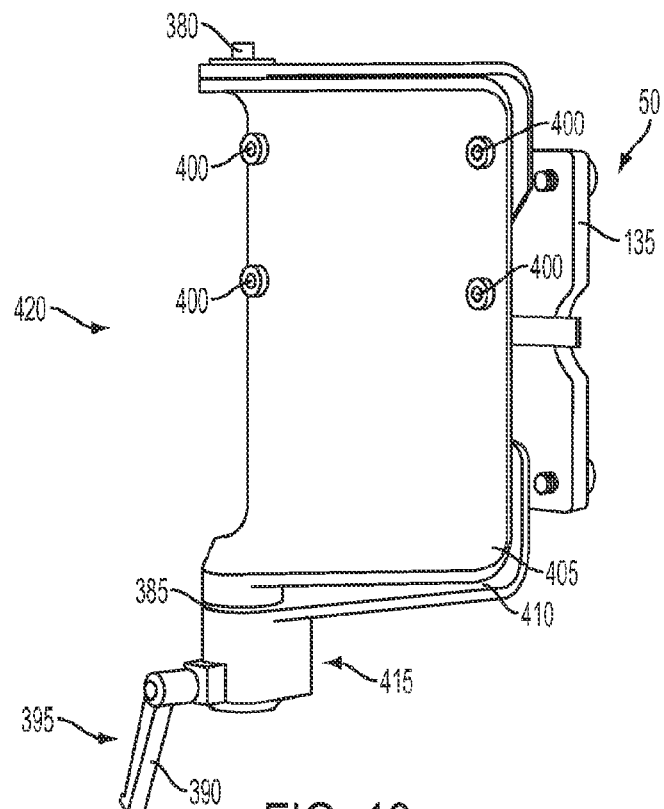
FIG. 19 depicts a perspective view of a swivel mount according to one or more embodiments shown and described herein.
Figure 20:
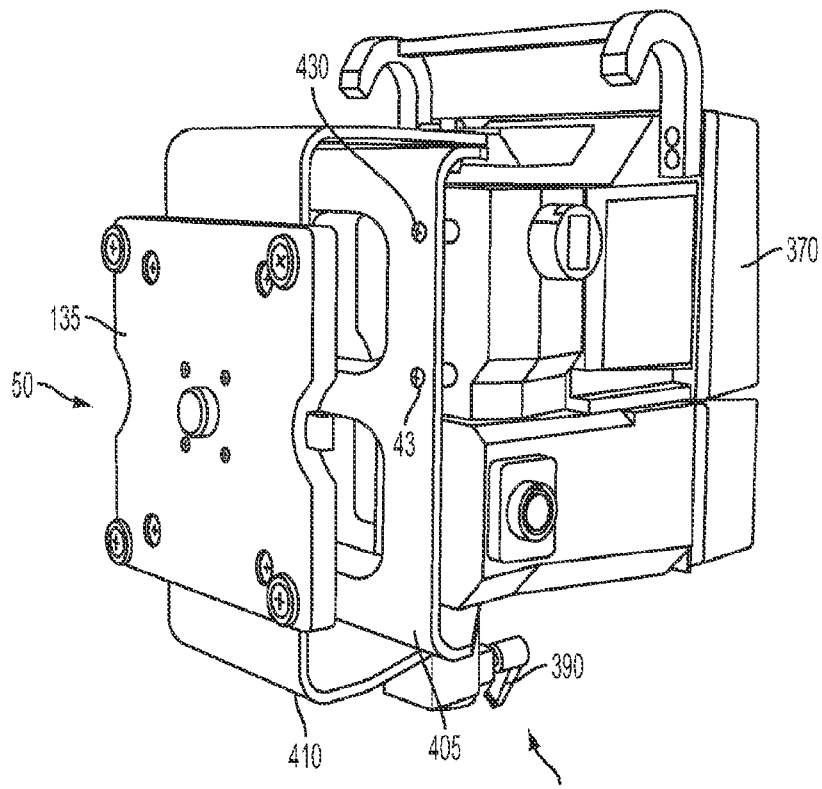
FIG. 20 depicts another perspective view of the swivel mount according to one or more embodiments shown and described herein.

FIGS. 19 and 20 are perspective views of a swivel mount 420. The swivel mount 420 comprises a swivel body 405 and a swivel frame 410. The swivel frame 410 is attached to the mounting plate 135 of the mount 50. The swivel frame 410 connects to the swivel body 415 through two hinges, an upper hinge 380 and a lower hinge 385, axially aligned along a longitudinal axis. The upper hinge 380 and the lower hinge 385 may allow the swivel body 405 to rotate up to 360 degrees in the swivel frame 410 about the longitudinal axis. The swivel body 405 may be locked from rotating via a lock body 415. The lock body 415 is a friction lock and comprises a threaded rod (not shown) that applies friction to the lower hinge 385 when a lock handle 390 is rotated. When friction is applied to the lower hinge 385, the swivel body 405 is held in place in an angular position relative to the swivel frame 410, enabling the swivel body 405 to be locked in any angular position about the longitudinal axis. Four swivel mounting holes 400 are located in the swivel body 405. The swivel mounting holes 400 are used to secure a piece of equipment 425 to the swivel body 410 via any fastening device 430 such as those set forth herein.

Figure 21:
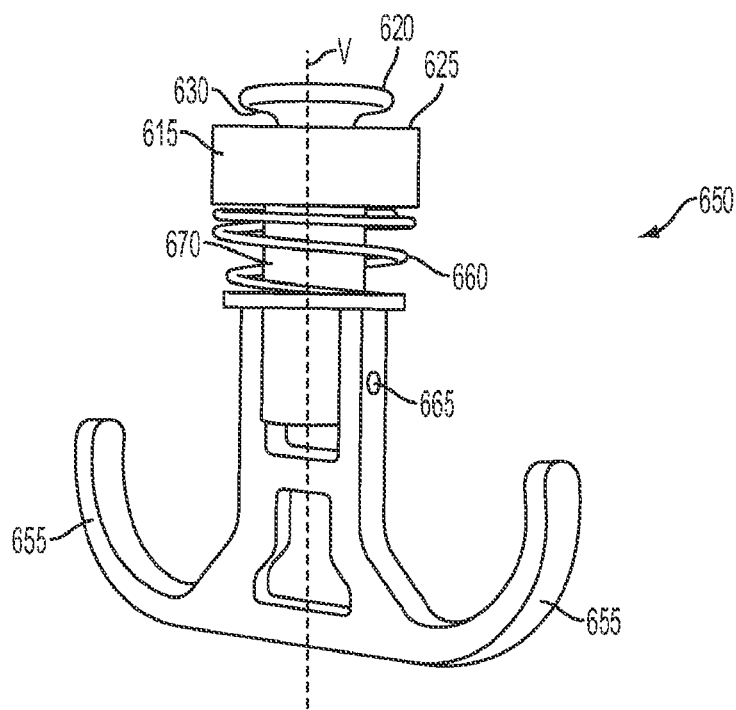
FIG. 21 depicts an overhead IV hook in a use position according to one or more embodiments shown and described herein.

FIG. 21 depicts an overhead IV hook 650 in a use position. The overhead IV hook 650 has two IV hooks 655. They are connected to a central shaft 670 via a locking hinge 665. The locking hinge is able to lock the two IV hooks 655 in either the use position or a storage position as shown in FIG. 21B. The locking hinge locks by a ball bearing biased into an indentation in a rotational element of the hinge, or by a tight fit within the hinge to cause friction to maintain the current position of the overhead IV hook 650. A release spring 660, the collar 615, and the central central shaft 670 are co-axially aligned along a vertical axis V. The release spring 660 is biased between the locking hinge 665 and the collar 615. The central shaft 670 is connected to the mount head 620. The overhead IV hook 650 is pressed against the track (e.g., track 10, FIG. 1) and aligned with one of the mounting holes (e.g., mounting holes 35, FIG. 1) on the track. As the overhead IV hook 650 is pressed against the track, the collar 615 compresses the release spring 600, the mount head 620 protrudes into the mounting holes and the overhead IV hook 650 is slid down into the necked down portion (not shown) and released. The collar engagement surface 625 and the mounting head engagement surface 630 clamp the track and secure the overhead IV hook 650 into place.

Figure 22:
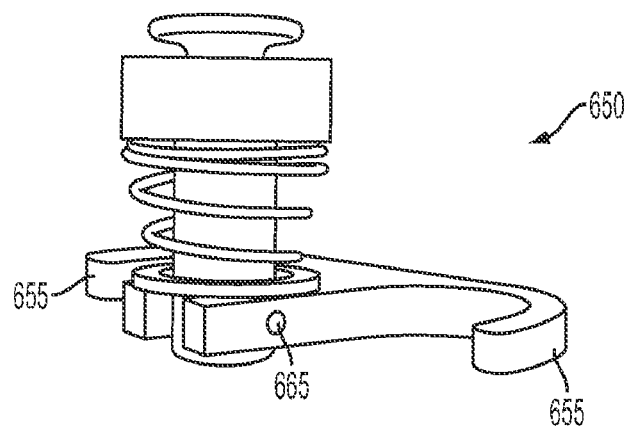
FIG. 22 depicts the overhead IV hook in the storage position according to one or more embodiments shown and described herein.

FIG. 22 depicts the overhead IV hook 650 in the storage position, e.g., the IV hooks 655 are rotated into a position parallel to the mounting plate (not shown). The locking hinge 665 maintains the storage position until moved to the use position (FIG. 21). In another embodiment, the IV hook 655 may be a utility hook, a tie down ring, a cleat, an eyelet, or a hook and loop fastener.

Figure 23A:
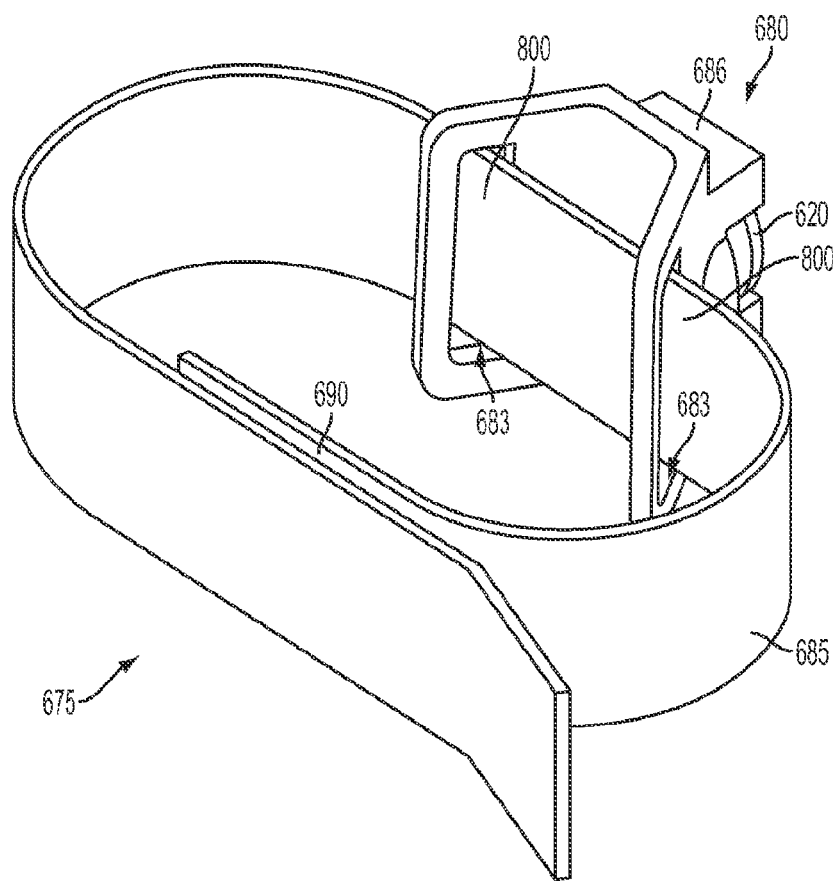
FIGS. 23A and 23B depicts an IV bag Velcro® wrap according to one or more embodiments shown and described herein.
Figure 23B:
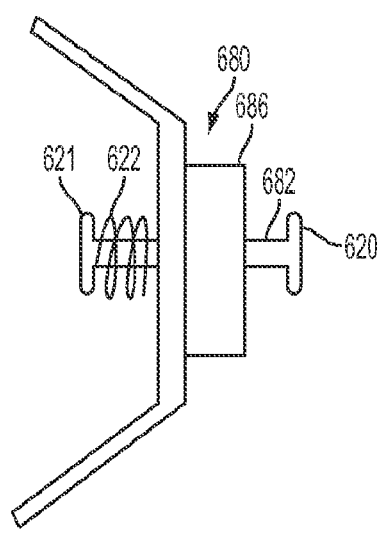

FIGS. 23A and 23B depict an IV bag Velcro® wrap 675 with a belt mount 680 and a belt 685. The belt 685 is threaded through two loop holes 800 to attach the belt 685 to the bracket 680. The belt mount 680 may include a shaft aperture disposed through the belt mount 680, at least one belt loop aperture 683, and a plurality of pressure arms 686 which are substantially parallel to each other. A second mount head 620 is coupled to a distal end a second shaft 682. A tab head 621 is coupled at the proximal end of the second shaft 682, the second shaft 682 is situated through the shaft aperture. A second bias spring 622 is coupled between the tab head 621 and belt mount 680, the second bias spring 622 biases the second mount head 620 against the belt mount 680. The belt 685 is coupled through the at least one belt loop aperture 683 and used to secure an IV bag (not shown) wherein the second release spring 622 is compressed by actuating the tab head 621 towards the belt mount 680 which will extend the second mount head 620 out past the plurality of pressure arms 686 and allow the IV bag Velcro® wrap to slideably engage a slot (20, 25, and/or 30) on the track 10.

The belt 685 can be made from any type of pliable material to include leather, rope (natural or synthetic), plastic products such as polymers, vinyl or rubber, and metal products such as thin aluminum band. The belt 685 is looped upon itself and secured using a secure strip 690. In the preferred embodiment, the secure strip 690 may be hook and loop (e.g., Velcro®) and can also be other types of fasteners such as buttons, snaps, etc. The IV bag Velcro® wrap 675 is used in conjunction with or without the overhead IV hook found in FIGS. 21 and 22. The IV bag Velcro® wrap is used to secure an IV bag (not shown) from hanging loosely. The IV hook 650 may be part of a kit including the track 10 from FIG. 1, the minitrack 12 of FIG. 38, or a quick mount track 11 from FIG. 28, the IV bag Velcro® wrap 675, and the IV hook 650.

Figure 24:
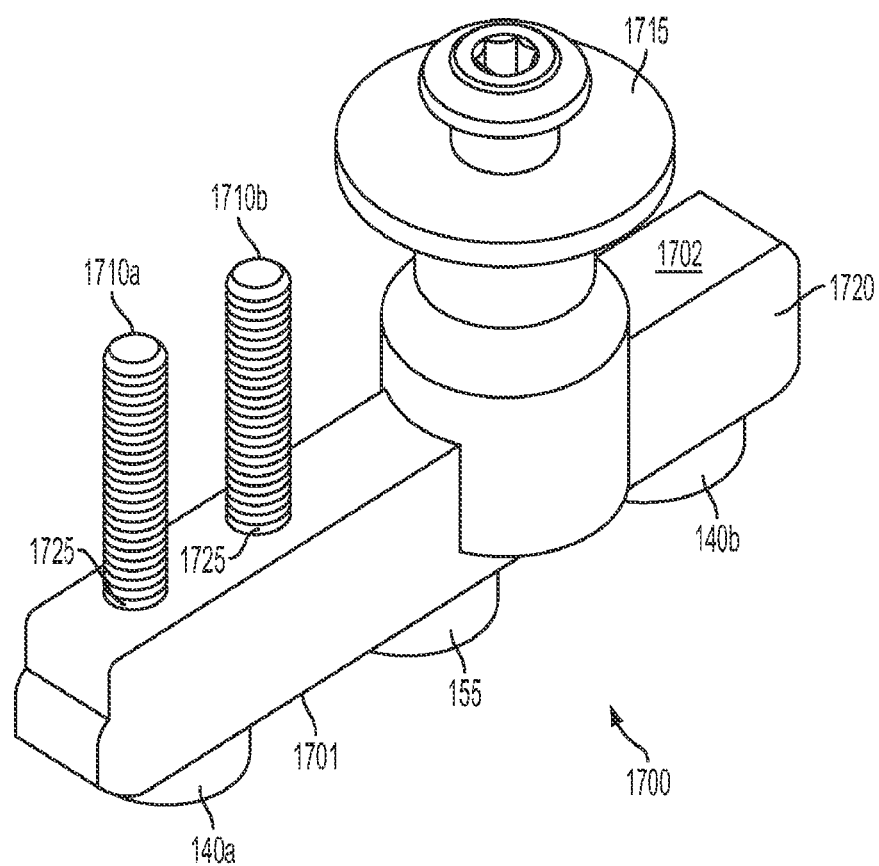
FIG. 24 depicts an equipment track mount according to one or more embodiments shown and described herein.

FIG. 24 depicts an equipment track mount 1700 including a rail 1720 with a track side 1701 and an equipment side 1702, a plurality of mount studs 140a and 140b coupled to the rail 1720. Individual ones of the plurality of mounting studs 140a and 140b may include a stem portion that extends outwardly from the track side 1701 and an enlarged head portion disposed at a distal end of respective stem portions. One or more threaded rods 1710a and 1710b coupled to the equipment side 1702, a locking pin 155 is disposed through the rail 1720 and extending outwardly from the track side 1701 in an extended position. A lock bias spring (not shown) is used to bias the locking pin 155 in the extended position. A control knob 1715 is coupled to the equipment side 1702 and operatively coupled to the locking pin 155 and when actuated, retracts the locking pin 155 into the rail 1720 and when released, allows the lock bias spring to bias the locking pin 155 in the extended position.

The equipment track mount 1700 is a universal mount that may be used on a variety of equipment to secure them to the track system. The equipment track mount 1700 has two mounting studs 140a and 140b positioned on the rail 1720 to engage the first outer slot 20 and the second outer slot 30 of the track 10 of FIG. 1, the minitrack 12 of FIG. 38, or the quick mount track 11 of FIG. 28A. Alternatively, each mounting stud 140a and 140b is spaced evenly to enable the equipment track mount 1700 to be secured either vertically or horizontally on the track 10, the minitrack 12, or quick mount track 11. In the preferred embodiment, the studs 1710 are threaded. The attachment points 1725 are areas of the rail 1720 where the attachment of a piece of equipment (not shown) are accomplished by conventional means to include a screw, bolt, stud, glue, post and cotter pin, or rivet. In the preferred embodiment, the stud 1710 is a threaded stud to allow the piece of equipment to be secured to the singe track mount 700 by a nut.

Figure 25:
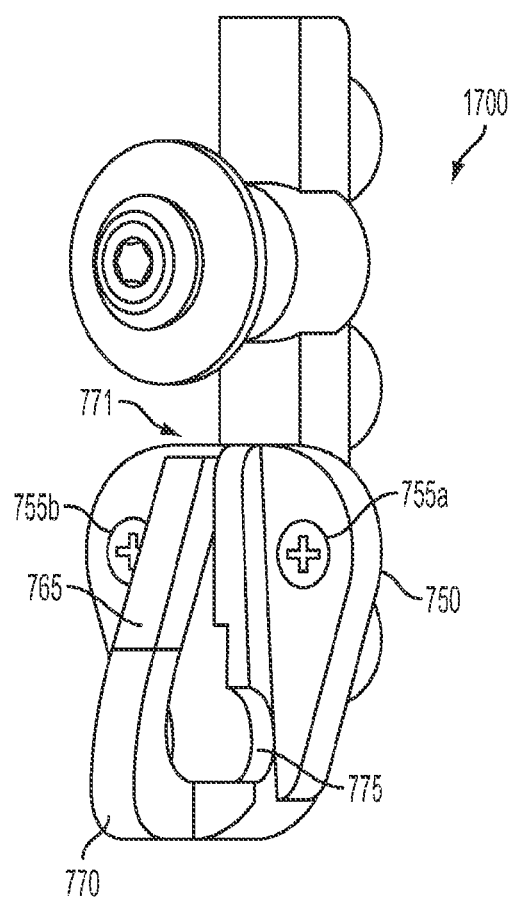
FIG. 25 depicts a retention hook according to one or more embodiments shown and described herein.

FIG. 25 depicts a retention hook 760 and equipment track mount 1700. A support plate 750 is attached the equipment track mount 1700 by screws 755a and 755b. The retention hook 760 a hook 770 and cradle 775 to capture and support the weight of an IV bag (not shown) or a strand of material just a handle of a bag or rope. A retention clip 765 is used to ensure the IV bag does not slip off the hook 700 and is hingedly coupled at base 771 of the hook 770. The retention hook 750 can suspend any item with a loop of correct size to slip over the hook 700 and fit under the retention clip 765 and in the cradle 775.

In another embodiment, a double mount plate (not shown) may be coupled to the threaded rods 1710a and 1710b of the equipment track mount 1700. The double mount plate may be a plate material that positions two or more retention hooks 760 side by side. This would allow more than one item to be hung or alternatively, allow for one heavy item to be hung by threading a strand of material through both hooks.

In yet another embodiment, a task light or lamp assembly may be secured to the equipment track mount 1700 and used to provide lighting in an enclosed area. The task light is attached to a lamp assembly mount via a clamp and a post (not shown) inserted into a flexible neck of the task light or lamp assembly. The lamp assembly mount is attached to the equipment track mount via the use of two nuts on the threaded rods 1710a and 1710b. The task light embodiment is not limited to a light. The flexible neck may allow the attachment of other instrument besides a light such as, for example, a magnifying glass, flashlight, minor, reflector, or a clip or claw to hold another instrument.

Figure 26:
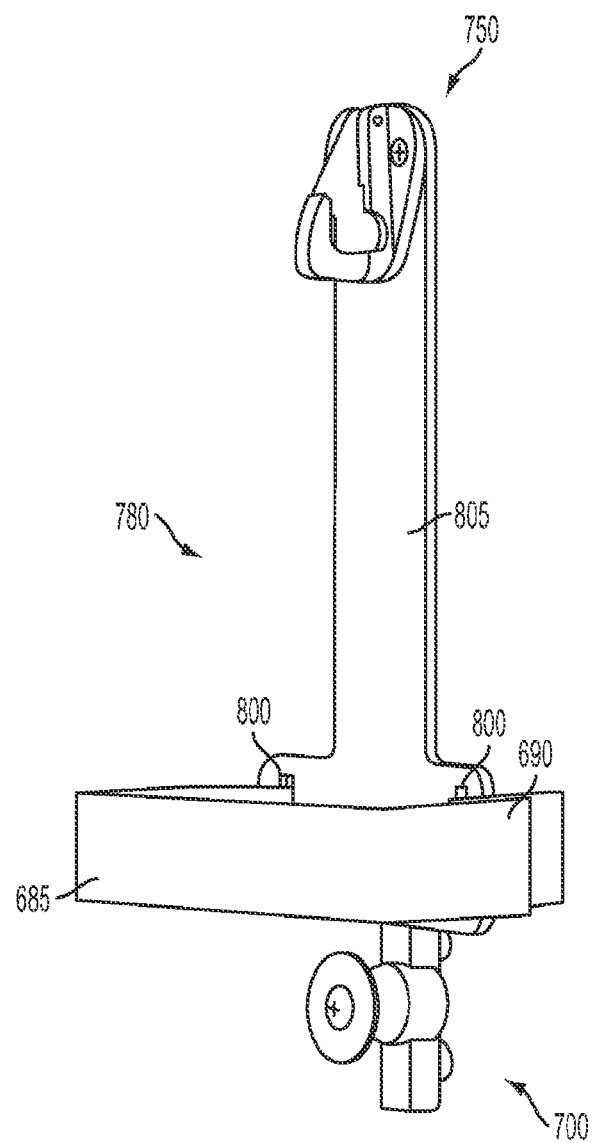
FIG. 26 depicts an IV bag mount according to one or more embodiments shown and described herein.

FIG. 26 depicts an IV bag mount 780 with a retention hook 750 at the top of a mast 805. The mast 805 may be attached to the bracket 680 of the IV bag Velcro® wrap 675 from FIG. 23. The mast may be attached to the equipment track mount 700. The IV bag (not shown) is hung from the retention hook 750 and secured against the mast 805 via the belt 685 threaded through two loop holes 800 and the secure strip 690.

Figure 27:
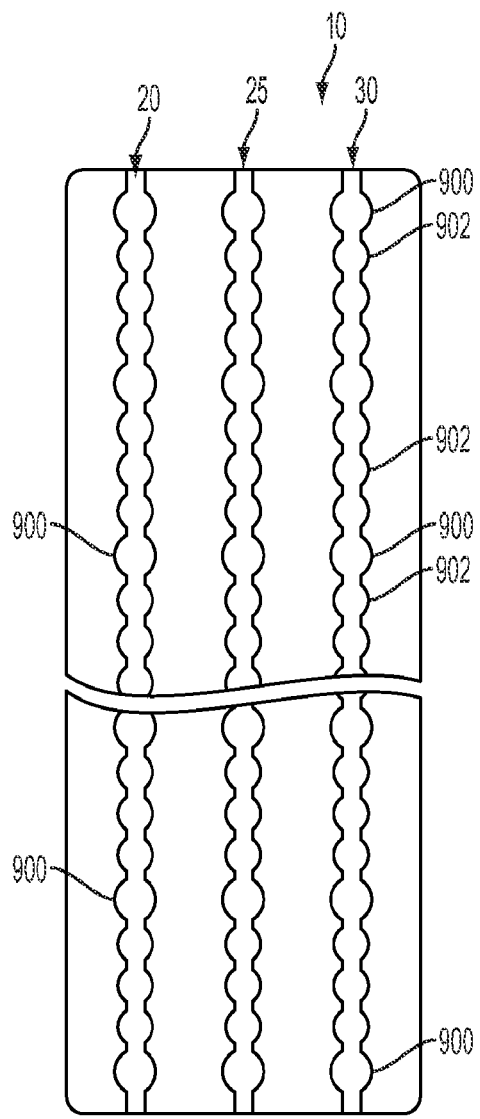
FIG. 27 depicts the track with a plurality of target open regions and non-target open regions according to one or more embodiments shown and described herein.

FIG. 27 depicts the track 10 with a plurality of target open regions 900 and non-target open regions 902. The first outer slot 20 and the second outer slot 30 may include the target open regions 900 to accommodate the mounting stud 140 of FIG. 3 or similar studs as for example the second mount head 620 of FIG. 21. In some embodiments, the target open regions 900 allow the mount 50 with a piece of equipment attached to it to slideably couple with the track 10 without the need for line of sight alignment of the mounting studs 140 with the open regions 35 of FIG. 1. The target open region 900 are larger in diameter and/or size than the non-target open regions 902, which allows for more variability in the orientation of the mount 50 to the track 10 and still enables the correct engagement between the track 10 and the mount 50. In alternative embodiments (not shown), the track 10 may not include the non-target open regions 902. It may include only a certain number of the target open regions 900 along tracks 20 and 30 and a neck down region running between the certain number of target open regions 900. An example of this embodiment is found in FIGS. 28A and 28B.

Figure 28A:
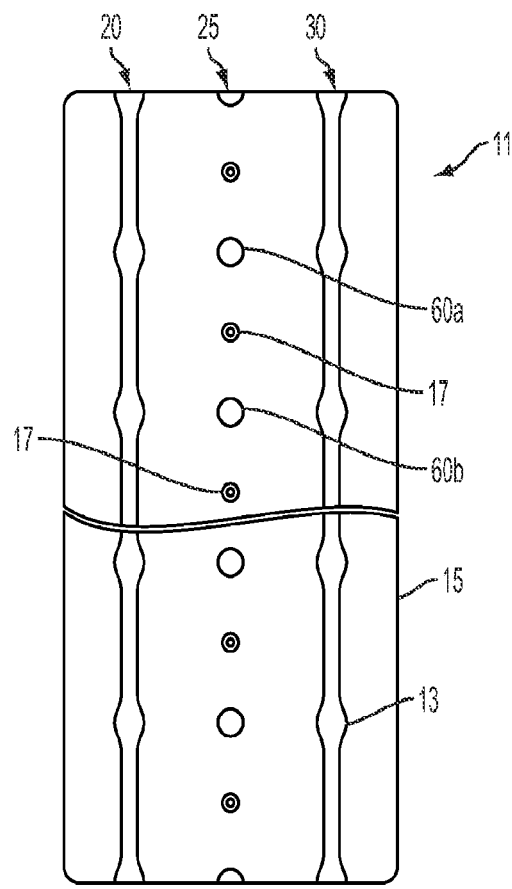
FIGS. 28A and 28B depicts a quick release track according to one or more embodiments shown and described herein.
Figure 28B:
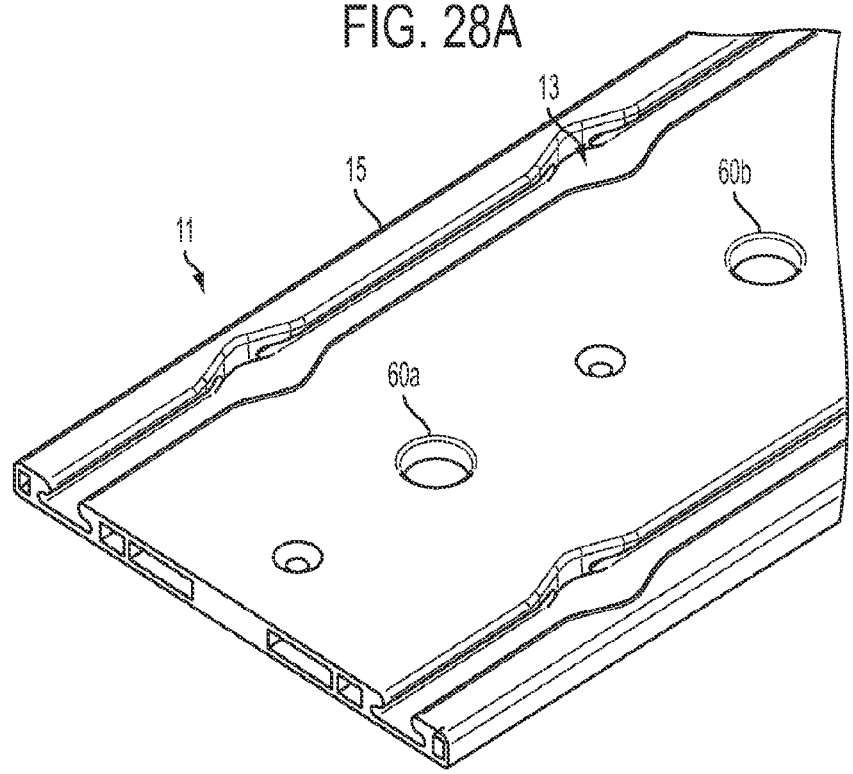

FIGS. 28A and 28B depict the quick mount track 11. The quick mount track 11 includes a backing plate 15 with a center slot 25, a first outer slot 20, and a second outer slot 30. The first outer slot 20 and the second outer slot 30 comprise a plurality of diamond contour target regions 13 that allow a round head of a t-shaped stud or mounting stud 140 of FIG. 3 to engage the first outer slot 20 and the second outer slot 30 at an angle to the backing plate 15. The center slot 25 has a plurality of locking pin apertures 60 (e.g. 60a and 60b) in the backing plate 15. The locking pin apertures 60 are in horizontal alignment with the plurality of diamond contoured target regions 13. the plurality of diamond contoured target regions 13 allow a mount 50 of FIG. 3 to be mounted to the quick mount track 11 with a degree of misalignment that may come from the inability to see and align the mount 50 to the open regions 35 of the track 10 of FIG. 1. The mount 50 may be rotated slightly in relation to the quick mount track 11 and still the mounting studs 140 will engage the plurality of diamond contoured target regions 13. As the mounting studs 140 are inserted into plurality of diamond contoured target regions 13, the mount 50 will align to be parallel with quick mount track 11. In other words, the plurality of diamond contoured target regions 13 allow for some rotation in the mount 50 and still enable a successful engagement of the first outer slot 20 and the second outer slot 30.

Furthermore, the plurality of diamond contoured target regions 13 will allow for mount 50 to be inserted into the quick mount track 11 at an angle to the backing plate 15. In other words, a user may insert the mounting studs 140a and 140b into the first outer slot 20 first before rocking or aligning the mount 50 so that the mounting studs 140c and 140d engage the second outer slot 30. This functionality allows for a user to mount a heavy or bulky piece of equipment with the need for a second user's help and allow for some misalignment (both rotation and angle) of the mount 54 in relation to the backing plate 15. The backing plate 15 may also have a plurality of mounting locations 17 to allow for fastening devices to secure the quick mount track 11 to a surface, wall, or structure.

Figure 29:
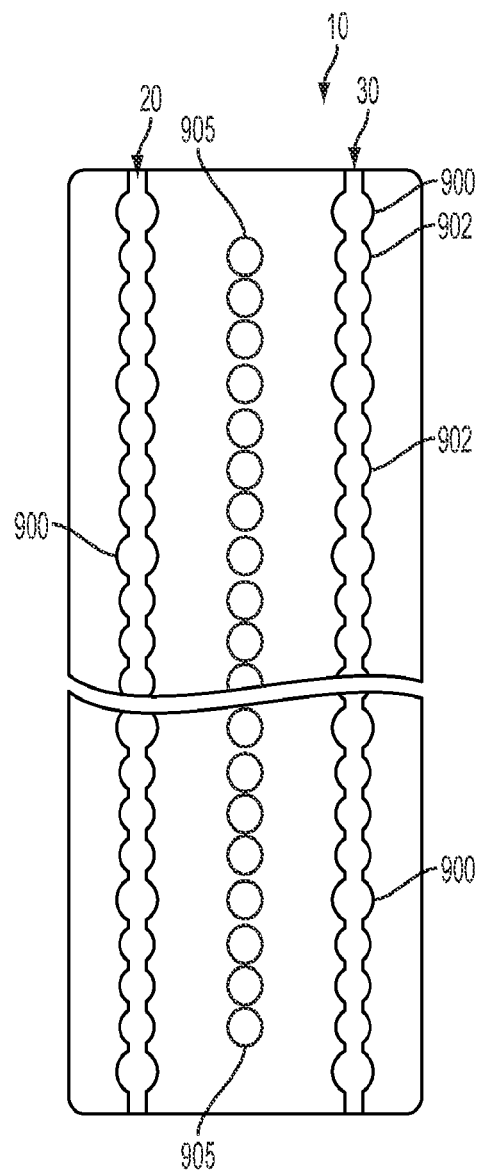
FIG. 29 depicts the track with a plurality of lock holes according to one or more embodiments shown and described herein.

FIG. 29 depicts the track 10 with a plurality of lock holes 905. The center slot 25 as shown in FIG. 1 may be replaced with the plurality of lock holes 905 to allow the locking pin 155 of FIG. 3 to slideably couple an individual lock hole 905 to secure the mount 50 to the track 10. In some embodiments, the first outer slot 20 and the second outer slot 30 may have the plurality of target open regions 900 as shown in FIG. 27, but they are not required or the plurality of diamond contoured target regions 13 as shown in FIGS. 28A and 28B.

Figure 30:
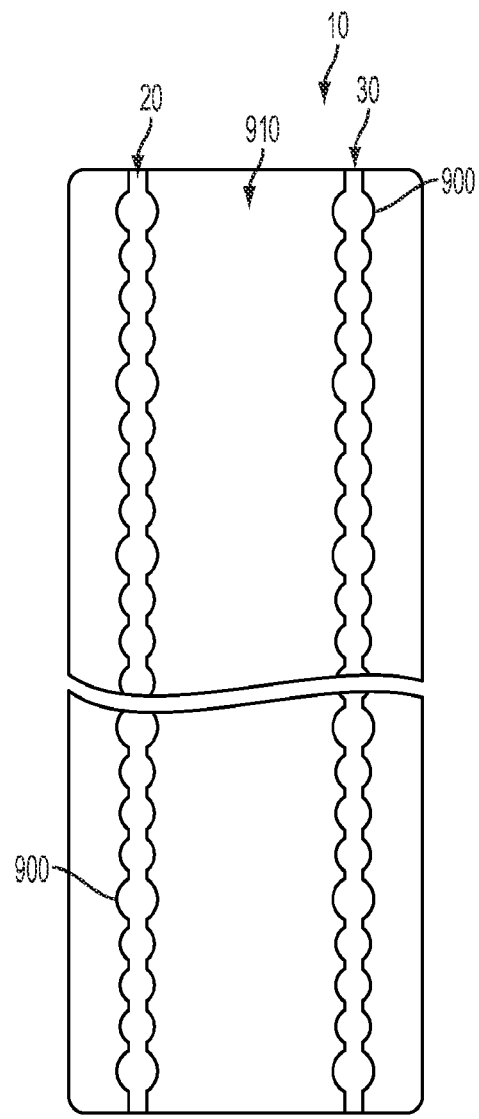
FIG. 30 depicts the track without a center slot according to one or more embodiments shown and described herein.

FIG. 30 depicts the track 10 without a center slot 25 as shown in FIG. 1. The first outer slot 20 and the second outer slot 30 may have the plurality of target regions 900 but they are not required as shown in FIG. 27 or the plurality of diamond contoured target regions 13 as shown in FIGS. 28A and 28B. A flat surface 910 allows for the locking pin 155 of FIG. 7 to apply a biasing force to an even surface to create an interference fit between the mounting studs 140 and the necked down regions 40 of the first outer slot 20 and the second outer slot 30. The biasing force exerts a force to separate the mount 50 from the track 10. The interference fit or friction fit of the mounting stud 140 pressing against the slots (20, 25, and 30), is a fastening device that fastens two parts by friction after the parts are pushed together. Furthermore, the snubber function outlined below in FIG. 37 may also provide the necessary force to secure the mount 50 to the track 10 of FIG. 30.

Figure 31:
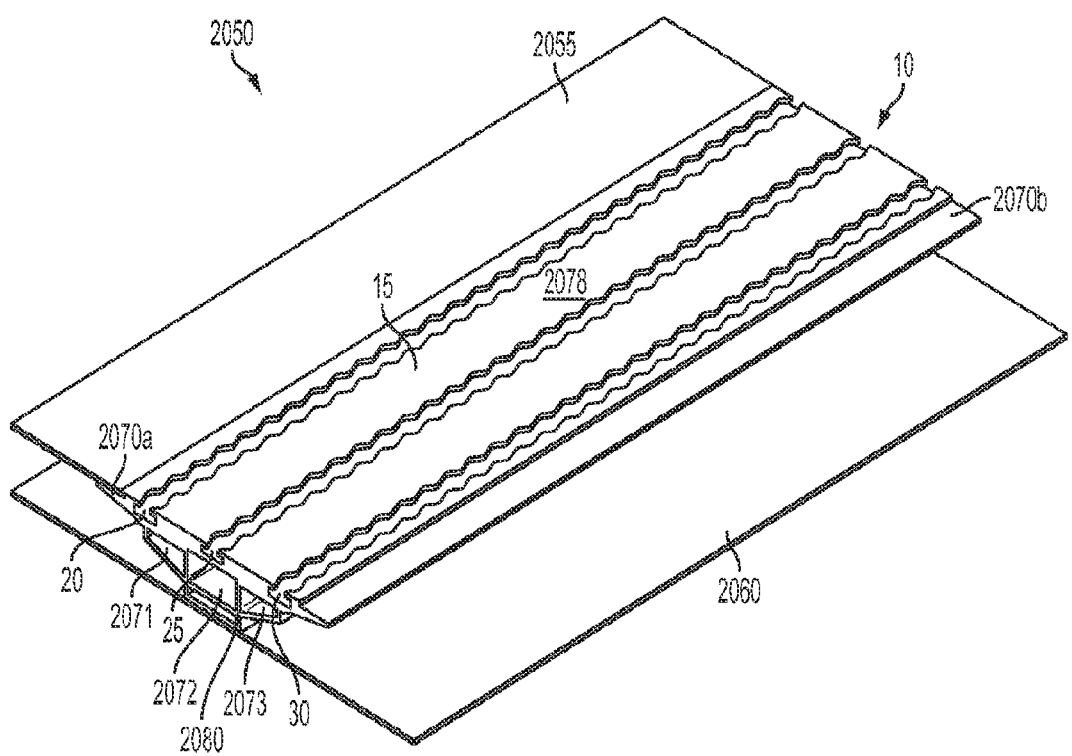
FIG. 31 depicts a wall assembly incorporating the track according to one or more embodiments shown and described herein.
Figure 38:
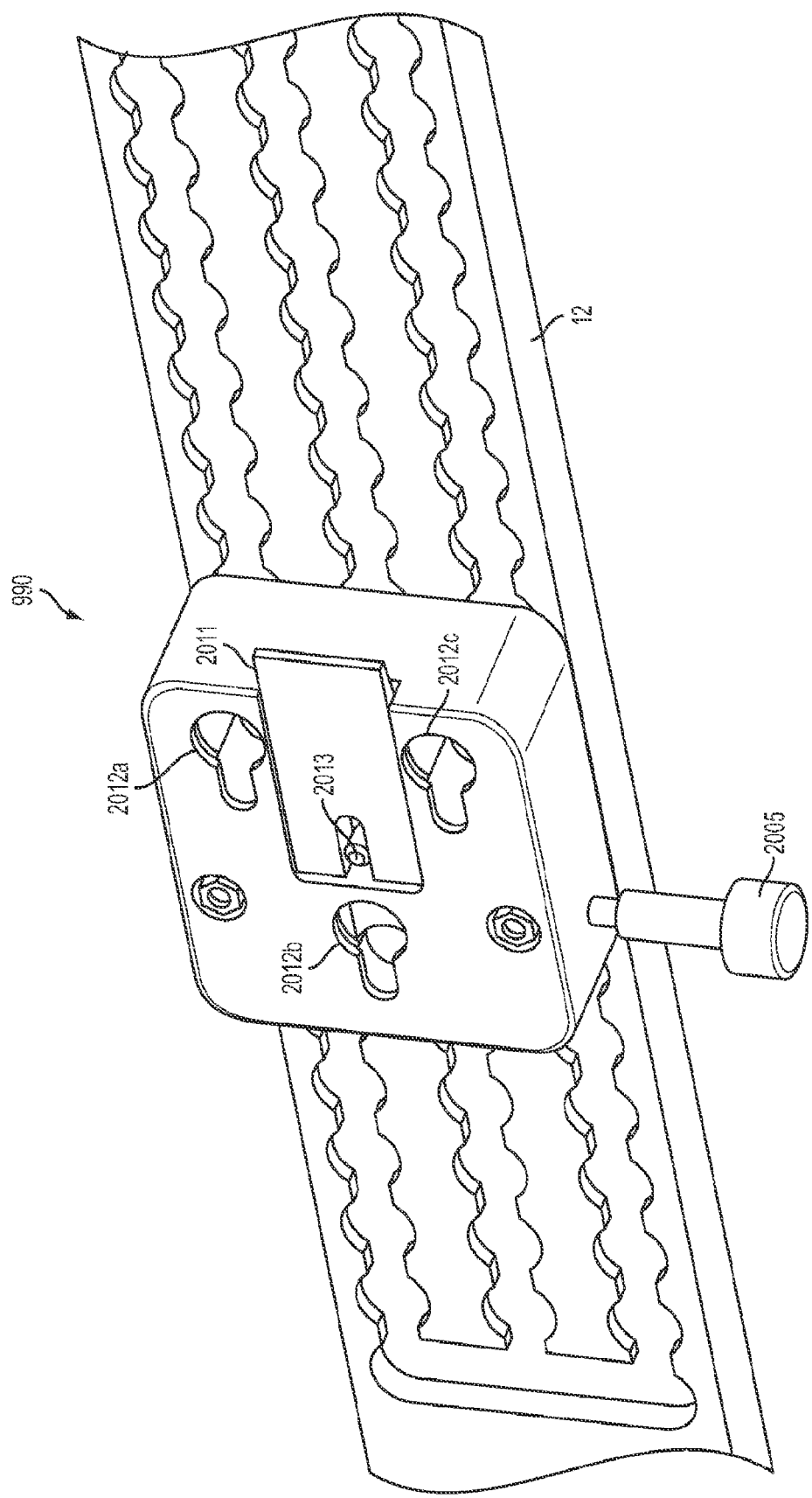
FIG. 38 depicts another embodiment of universal adaptor according to one or more embodiments shown and described herein.

FIG. 31 depicts a wall assembly 2050 incorporating the track 10 of FIG. 1, the minitrack 12 of FIG. 38, or the quick mount track 11 of FIG. 28. The track 10 may include a plurality of tabs 2070a and 2070b. The plurality of tabs 2070a and 2070b are shown running the long dimension of the track 10 but it should be understood that the plurality of tabs 2070a and 2070b may also run the short dimension of the track 10. The plurality of tabs 2070a and 2070b may support a wall covering 2055 and keep the wall covering 2055 flush with the face surface 2078 of the backing plate 15. The wall covering 2055 may be made of any material and may be fastened to the plurality of tabs 2070a and 2070b through welding, adhesives, or the fastening devices described above. An outer wall covering 2060 may also be made of any material and may be fastened to a support structure 2080 through welding, adhesives, or the fastening devices described above. The support structure 2080 is coupled to the backing plate 15 and provide strength and rigidity to support the backing plate 15, the wall coverings 2055, and the outer wall covering 2060. The support structure 2080 may also be part of a frame of a larger wall assembly 2050. A first outer channel 2071, a center channel 2072, and a second outer channel 2073 may be part of the support structure 2080 and provide conduits for electrical wiring, plumbing, and other services that may be provided by the wall assembly 2050.

A backing plate 15 with a face surface 2078 and a back surface, the face surface is opposite of the back surface. The backing plate 15 includes a first outer slot 20 with a plurality of open regions and a plurality of necked down regions connecting the plurality of open regions, a second outer slot 30 with the plurality of open regions and the plurality of necked down regions connecting the plurality of open regions, and a center slot 25 with a plurality of locking pin apertures in the backing plate, the locking pin apertures are in horizontal alignment with the plurality of open regions of the first outer slot 20 and the second outer slot 25. The backing plate 15 also includes a first trim tab 2070a along a first outer edge of the backing plate 15 to support a first wall covering 2055 flush with the face surface 2078 of the backing plate 15, and a second trim tab 2070b along a second outer edge of the backing plate 15 to support a second wall covering 2055b of FIG. 32 flush with the face surface 2078 of the backing plate 15. A support structure 2080 coupled to the back surface of the backing plate 15 to provide support for the wall assembly 2050 wherein the wall assembly 2050 includes structure for supporting the first wall covering 2055, the second wall covering, and an outer wall covering 2060.

Figure 32:
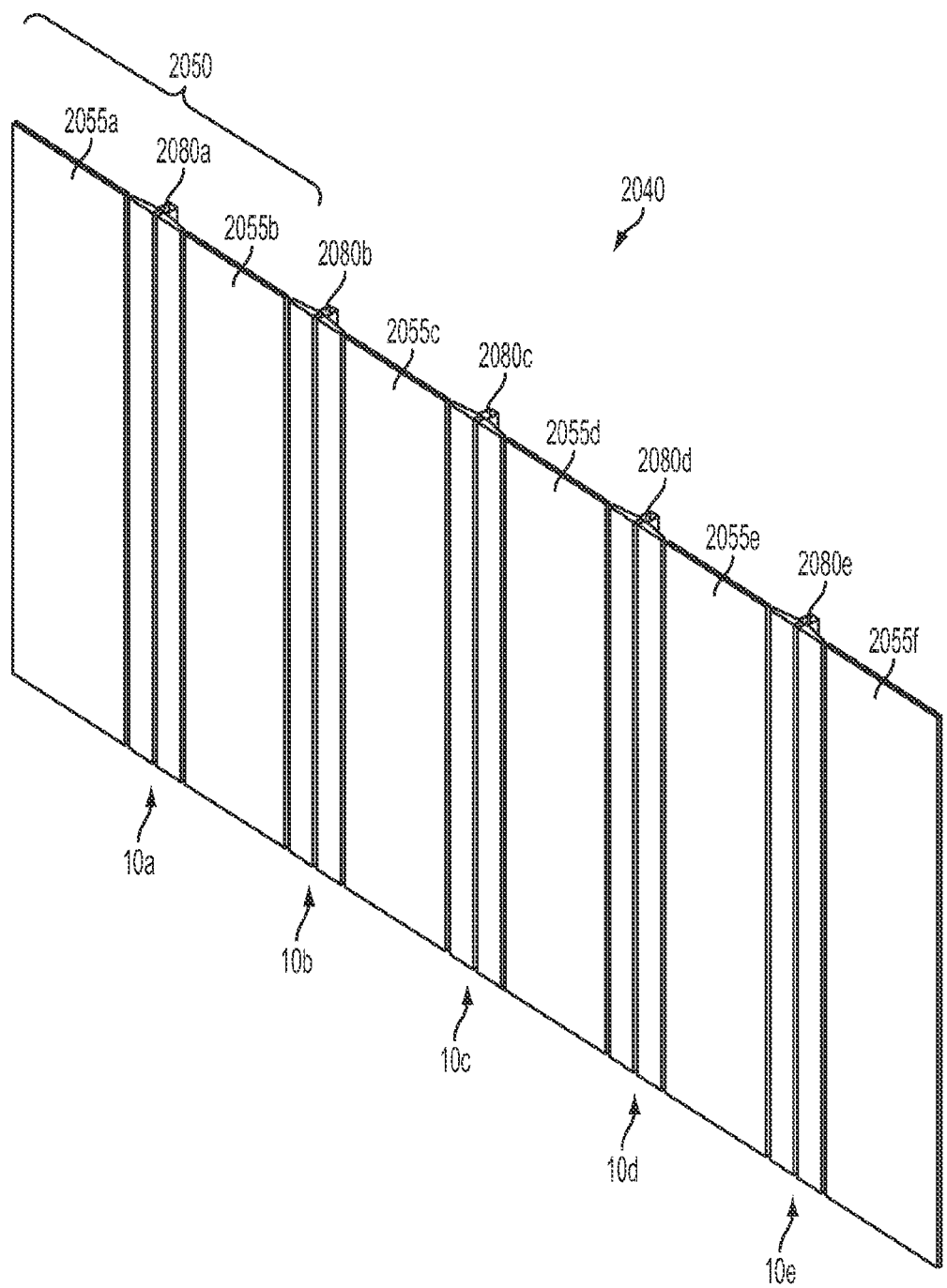
FIG. 32 depicts a plurality of wall assemblies chained together according to one or more embodiments shown and described herein.

FIG. 32 depicts a wall 2040. The tracks 10a, 10b, 10c, 10d, and 10e may be spaced along the wall 2040 at any interval desired depending on the type and number of the pieces of equipment to be mounted to the wall 2040. The wall comprises a plurality of wall assemblies 2050 chained together. The wall coverings 2055a, 2055b, 2055c, 2055d, 2055e, and 2044f coupled the tracks 10a, 10b, 10c, 10d, and 10e together. It should be noted that the wall coverings 2055a, 2055b, 2055c, 2055d, 2055e, and 2044f may provide structural support for the tracks 10a, 10b, 10c, 10d, and 10e, they are not required to as the structural support 2080a, 2080b, 2080c, 2080d, and 2080e provide the foundation for the support of the wall 2040.

Figure 33:
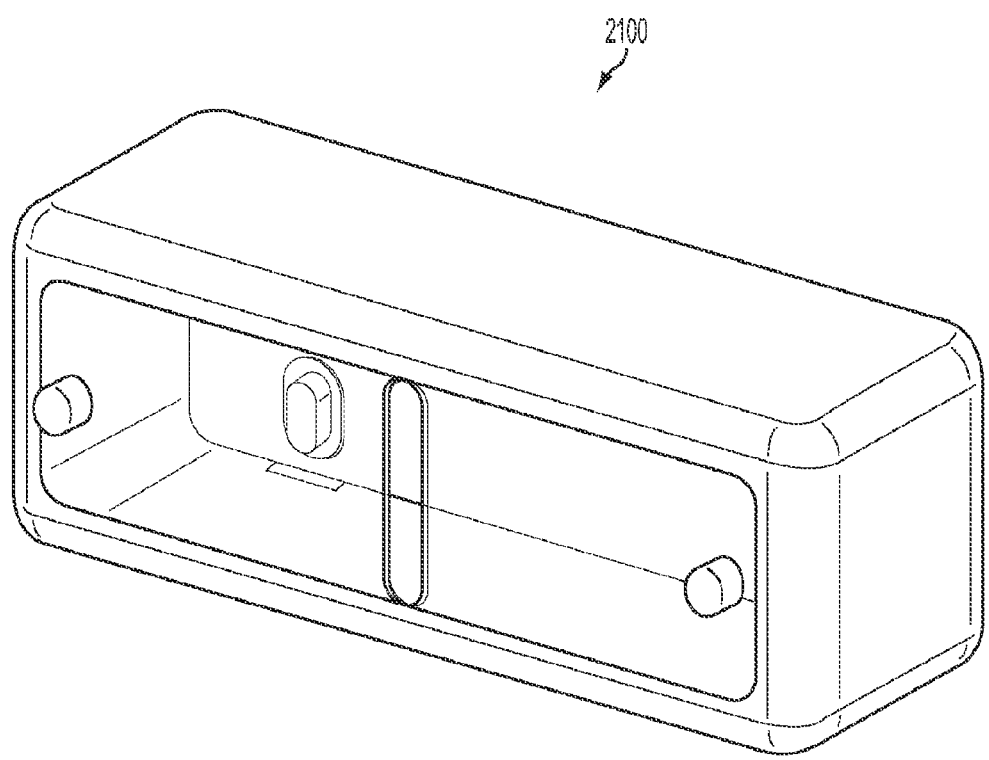
FIG. 33 depicts a cabinet for use on the wall according to one or more embodiments shown and described herein.

FIG. 33 depicts a cabinet 2100 for use on the wall 2040 of FIG. 32. The cabinet 2100 may be used to store items along the wall 2040.

Figure 34:
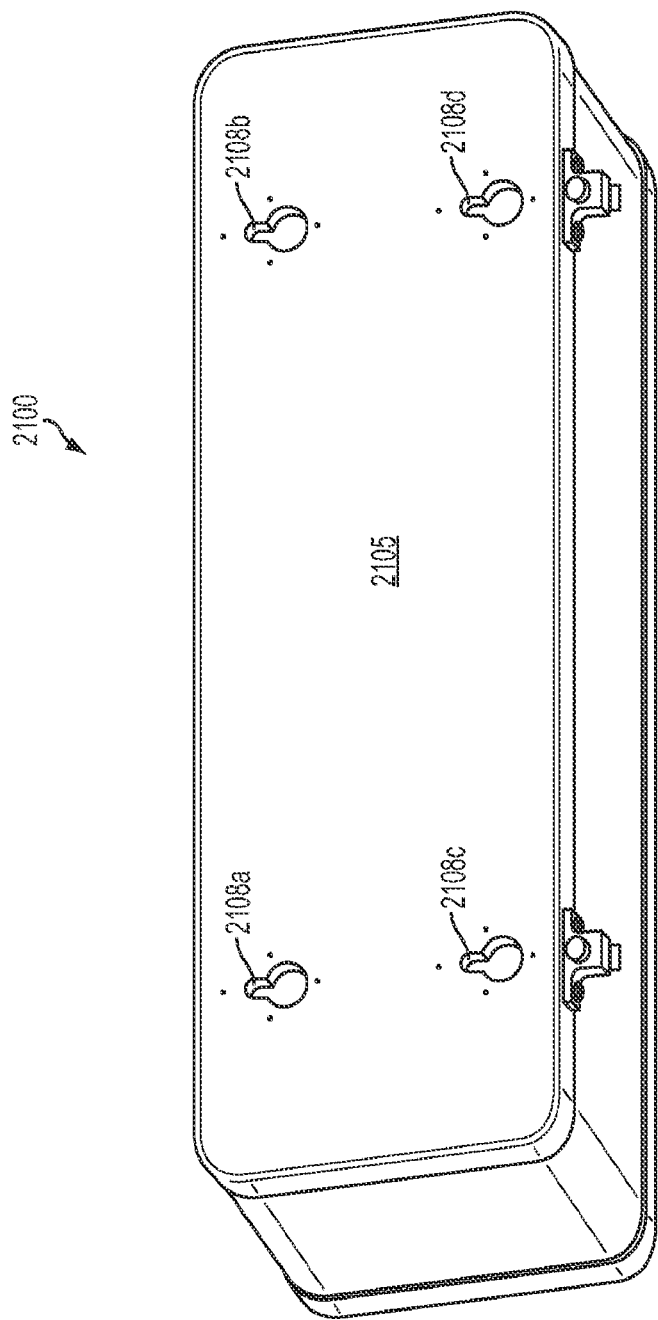
FIG. 34 depicts a backside of the cabinet according to one or more embodiments shown and described herein.

FIG. 34 depicts a backside 2105 of the cabinet 2100. The plurality of keyholes 2108a, 2108b, 2108c, and 2108d may be used to engage a single track stud as described above in relation to FIG. 9. The single track studs may be positioned anywhere along the track 10a, 10b, 10c, 10d, and 10e of FIG. 32 as long as they are position to engage the plurality of keyholes 2108a, 2108b, 2108c, and 2108d on the backside 2105 of the cabinet 2100.

Figure 36:
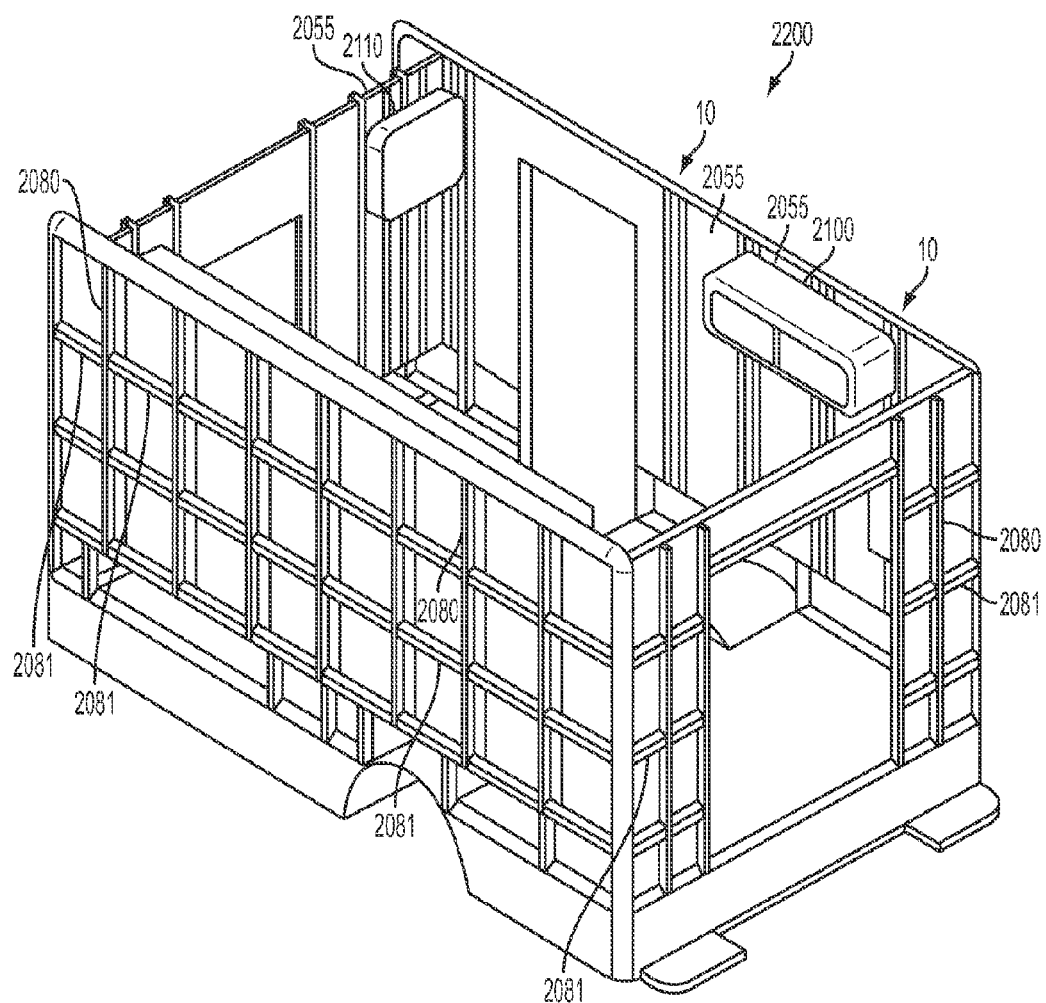
FIG. 36 depicts a vehicle cab according to one or more embodiments shown and described herein.

As described above, a mount 50 of FIG. 3, an adaptor of FIG. 8, or a wedge mount 47 of FIG. 11 may be used to secure the cabinet 2100 or the case 2110 of FIG. 36 to the track 10.

Figure 35:
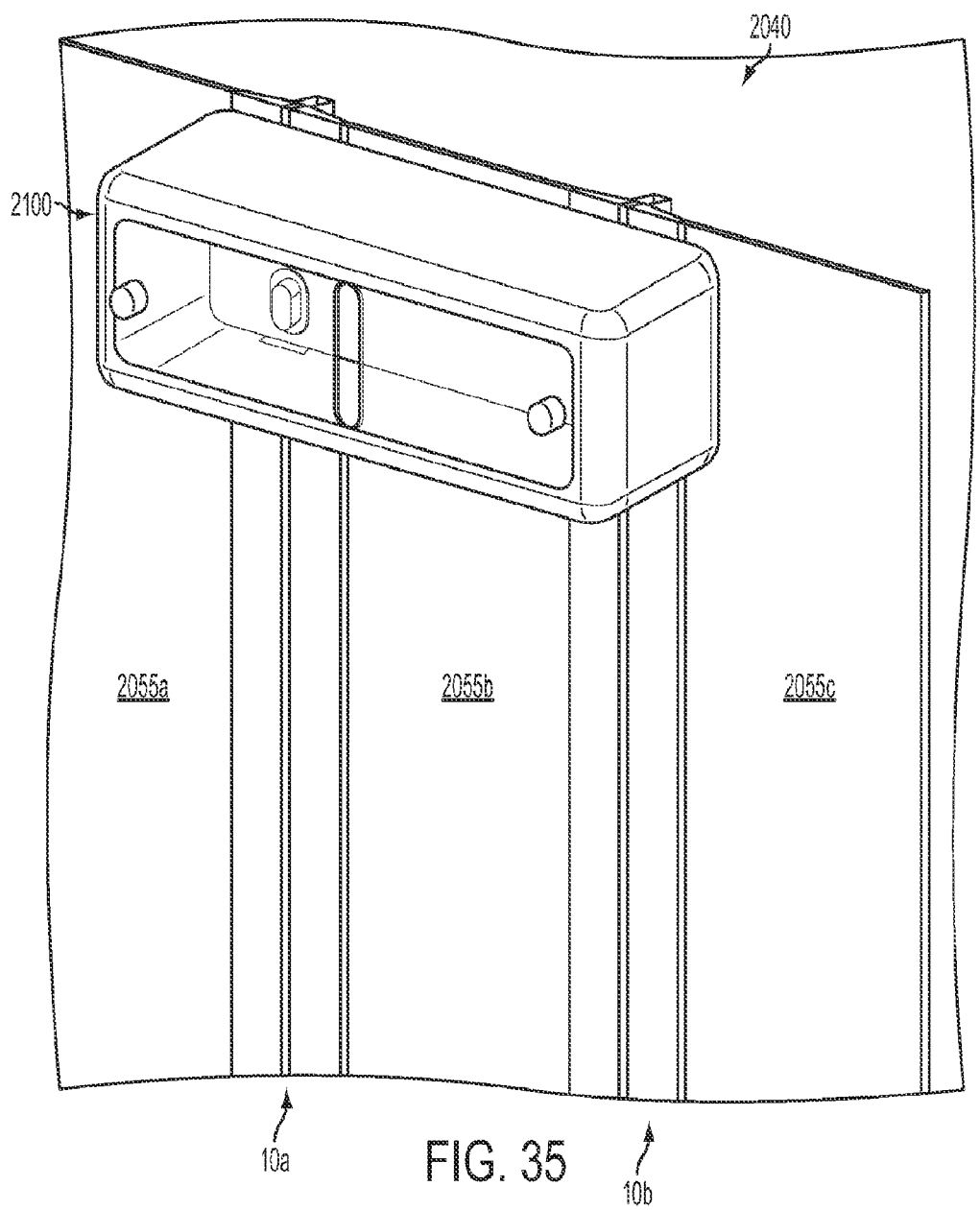
FIG. 35 depicts the cabinet mounted to the wall according to one or more embodiments shown and described herein.

FIG. 35 depicts the cabinet 2100 mounted to the wall 2040 of FIG. 32. In this embodiment, the tracks 10a and 10b are spaced to allow a single track stud or the like to engage the plurality of keyholes 2108a, 2108b, 2108c, and 2108d on the backside 2105 of the cabinet 2100 as shown in FIG. 34. The wall coverings 2055a, 2055b, and 2055c provide a flush surface for the wall 2040 and the cabinet 2100.

FIG. 36 depicts a vehicle cab 2200. In this embodiment, the support structure 2080 provides the framework for the vehicle cab 2200. Cross members 2081 are added between the support structure 2080 to add additional strength and rigidity to the vehicle cab 2200. The support structure is coupled to the track 10 as shown in FIG. 31 and wall coverings 2055 span the distance between each track 10 to provide a flush inner surface for the vehicle cab 2200. A cabinet 2100 is shown attached to the tracks 10 as wells a case 2110. The case may also include plurality of keyholes on its backside and mount to the track in a similar fashion as the cabinet 2100.

The vehicle cab 2200 but it should be understood that the any walled enclosure may incorporate the wall assembly 2050 of FIG. 31. Furthermore, the tracks 10 are shown vertical in the vehicle cab 2200 however they may also run horizontal and use the cross members 2081 in place of the support structure 2080. An outer wall covering 2060 may also be used to cover the vehicle cab 2200.

Referring to FIGS. 3, 10B, 11, and 37, in one embodiment, the locking pin release 160a and 160b and the wedge release 61 may include a snubber function. The snubber function allows the locking pin release 160a and 160b and the wedge release 61 to take up any slack between the mount 50 and the track 10. For ease of mounting and unmounting the mount 50 to and from the track, the tolerance between the mounting studs 140 and the slots (20, 25, and 30) are loose or not very tight. Therefore, when mounted, the mount 50 may rattle or shake on the track 10, the minitrack 12, or quick mount track 11. The snubber function either uses a plunger (2020 of FIG. 10B) to apply a pressure between the mount 50 and the track 10 or it retracts the mounting studs 140 into the mounting plate 135 to take up the loose tolerance between the mount 50 and the track 10.

Figure 37:
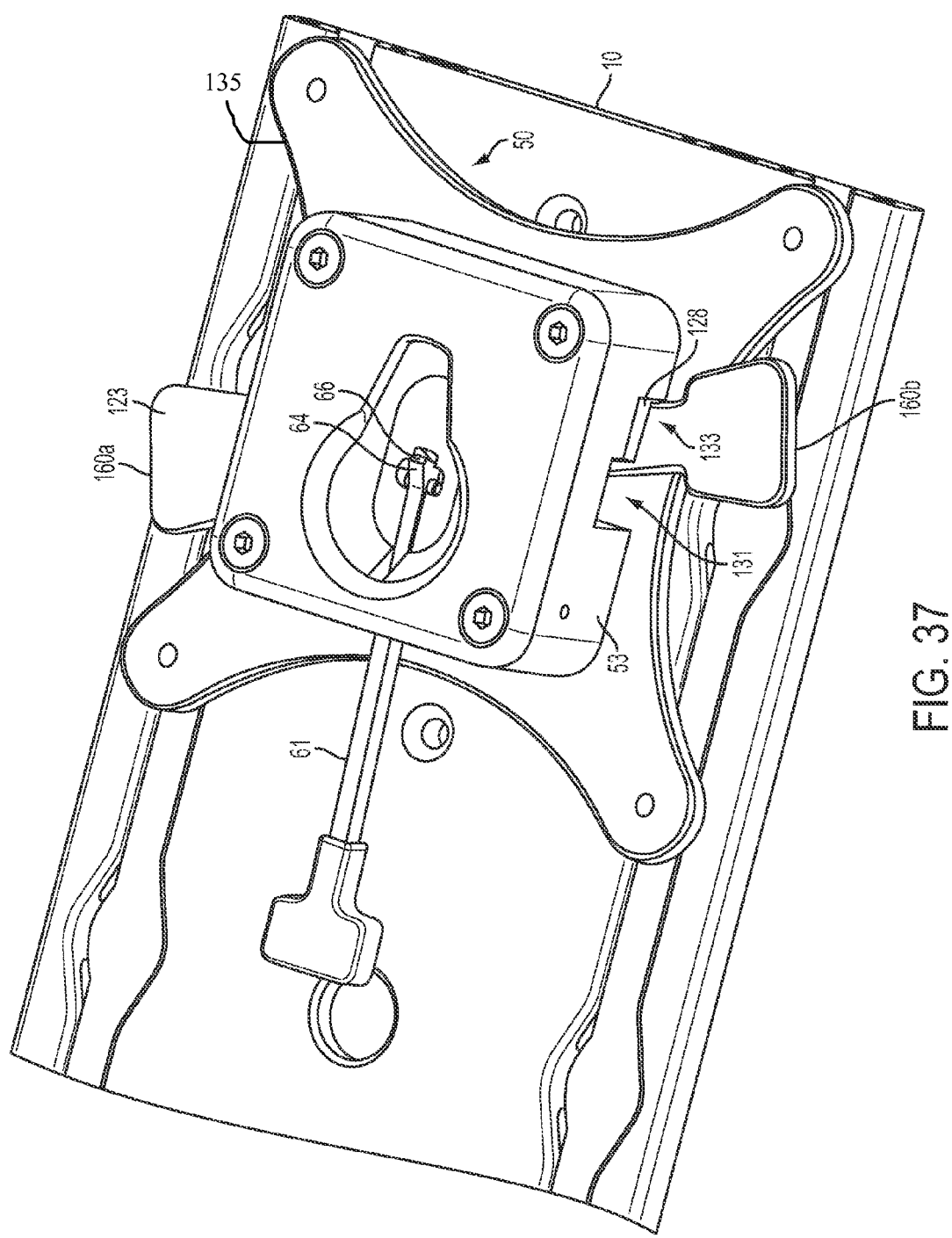
FIG. 37 depicts the wedge mount with a locking pin release that rotates about a central axis according to one or more embodiments shown and described herein.

Referring now to FIG. 37, the wedge mount 47 is shown with the locking pin release 160a and 160b (160) are a single unit and rotate about a central axis. The locking pin release 160 has a locked position 133 and an unlocked position 131. In the unlocked position 131, the locking pin release 160 is free to actuate towards or away from the track 10 to release the mount 50 from the track 10 as described above. In the locked position 133, a stop 128 prevents the towards and away movement of the locking pin release 160. As the locking pin release 160 is actuated (rotated) from the unlocked position 131 to the locked position 133, a cam (not shown) either presses a plunger (not shown) against the track 10 to take up the loose tolerance between the mount 50 and the track 10 or it retracts the mounting studs into the mounting plate 135 as described above in the snubber function.

Furthermore, in another embodiment, the blade 64 has a different shape from the blade 64 of FIG. 12 as well as the engagement surface 66. The narrower shape of the blade 64 and engagement surface 66 of FIG. 37 enables the wedge release 61 to absorb greater shock loads without breaking and conform to narrower wedge interfaces (not shown).

FIG. 38 depicts another embodiment of universal adaptor 990 of FIGS. 10A and 10B. A plurality of keyhole slot apertures 2012a, 2012b, and 2012c are shown to receive an equipment mount 172 (not shown), where the different embodiments of the equipment mount 172 are described above. The receiver equipment release 2005 releases the equipment mount 172 from the universal adaptor 990 through a set of release pins (not shown) in the civity of each of the plurality of keyhole slot apertures 2012a, 2012b, and 2012c. The paddle latch 2011 actuates a pull-out pin 2013 to release the universal adaptor 990 from the minitrack 12. The pull-out pin 2013 operates similarly to the locking pin 155 of FIG. 3.

The minitrack 12 is another embodiment of the track 10 of FIG. 1. The mintrack 12 enables a smaller load to be mounted to a surface, wall, or structure.

Figure 39A:
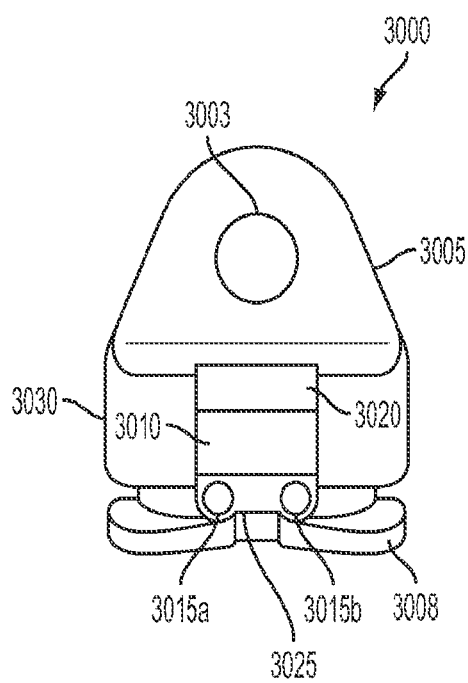
FIGS. 39A and 39B depict a quick release clip according to one or more embodiments shown and described herein.
Figure 39B:
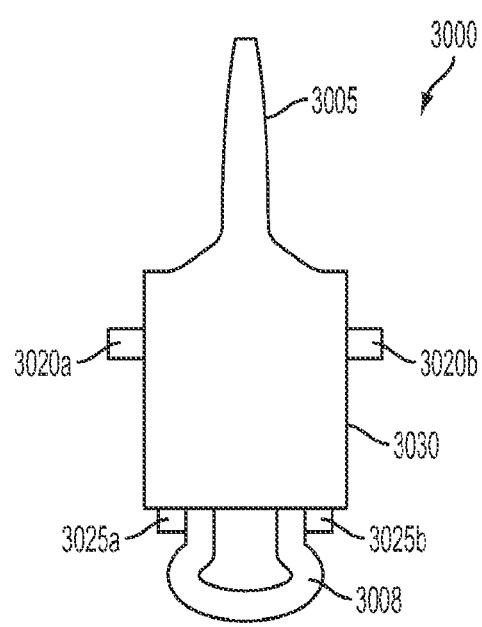

FIGS. 39A and 39B depict a quick release clip 3000. The quick release clip 300 has a eyelet structure 2005 with an eyelet aperture 3003. The eyelet aperture 3003 may allow a strand of material to hang from the quick release clip 3000, a latch, a clip, a rope or similar material, a carabiner or the like to couple with the quick release clip 3000. The foot structure 3008 mimics the footprint of two mounting studs 140 of FIG. 3 if they were placed in adjoining open regions 35 of the track 10 of FIG. 1. A clip pin 3025 is biased towards the foot structure 3008 and mimics the locking pin 155. A handle 3020 enables the clip pin 3025 to be pulled away from the foot structure 3008 to release the quick release clip 3000 from the track 10. A plurality of indents 3015*a* and 3015*b* allow the clip pin 3025 to lock the quick release clip 3000 between two necked down regions 40. In other words, when the quick release clip 3000 is in the out-of-phase position (refer to FIG. 5), the adjoining necked down regions 40 occupy the plurality of indents 3015*a* and 3015*b*. The clip pin 3025 includes both sides of the clip pin 3025*a* and 3025*b* as well as both sides of the handle 3020*a* and 3020*b* and they all move together as one piece.

When the quick release clip 3000 is inserted into the track 10 in the in-phase configuration, the clip pin 3025 contacts the face surface of the track 10 and does not occupy an open region 35. The quick release clip 3000 is slid to the out-of-phase configuration and the clip pin 3025 is biased to be extended into the open region 35, thereby locking the quick release clip 3000 to the track 10.

It should be appreciated that as used through the application the mounting studs 140 may be replaced with the tongue 180 to allow different mounting configurations to be used between all the embodiments. The size and orientation of the track 10 and modular plates 105 may vary depending on the application. The number of mounting studs 140 or track slots 20, 25, 30 may also vary depending on the application and load considerations. Furthermore, all the embodiment disclosed herein, to include for example the track 10, the fixed position mount 130, the mount 50, may be made from aluminum, steel, plastic, rubber, casting, or similar materials.

It will further be appreciated that the track system may be modular in that a number of components of the track system may be interchangeable, which can reduce assembly time, complexity, and costs. Such modularity in the track system may allow for a more rapid and fluid response to a particular situations, which may improve the outcomes in some instances. The track system configuration allows its use on a variety of different vehicles and/or other equipment, thus providing the benefit of interchangeability and flexibility. Another benefit of the track systems described herein is that they permit a user to install, remove, and/or reconfigure one or more pieces of equipment with little-to-no visibility as the track system can be employed by tactile sensing only (i.e., feel only).

It will further be appreciated that the track 10, the minitrack 12, and the quick mount track 11 may be scalable to accommodate different size and different configurations of mounting studs. For example, the standard size may be 19.05 mm (¾ inch) holes (open regions 35 of FIG. 1) on 25.4 mm (1 inch) center. The track 10, the minitrack 12, or quick mount track 11 may be increased to 38.1 mm (1.5") holes on 50.8 mm (2 inch) center. Alternatively, the track 10, the minitrack 12, or quick mount track 11 may be decreased to 9.5 mm (⅜ inch) holes on 12.7 mm (½ inch) center which would correspond to the minitrack 12 of FIG. 38.

In some embodiments, printed or painted indicia and/or tactile indicia (e.g. a location indicator) may be used along with the track system. For example, a location indicator may be placed alongside or even on the tracks 10. In some embodiments, a marker may be placed on the tracks 10 to allow for rapid adjustments of the antenna mount 100 with little to no visibility. The indicia may be located on the tracks 10 or on the military vehicle 300.

The track system can be made out of any material of sufficient strength. It could be made out of one piece of material or a casting. The studs on the mounting plate and the openings on the tracks can be increased or decreased as needed to reach the desired mounting strength required by the equipment and material used in the system's manufacture.

It will be appreciated that this system does not require tools to mount a piece of equipment to a vehicle or other equipment. As set forth above, the ease of its use and installation would allow the mounting of a piece of equipment in either daytime or nighttime operations. The track system is designed so that the quick releases can be found in the dark and the piece of equipment can be moved or removed under little-to-zero light conditions.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Certain terminology is used in the disclosure for convenience only and is not limiting. The words "left", "right", "front", "back", "upper", and "lower" designate directions in the drawings to which reference is made. The terminology includes the words noted above as well as derivatives thereof and words of similar import.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An equipment mount, comprising a mounting plate, a collar, a capture plate, a wedge release, a wedge bias spring, at least one mounting stud, and a release mechanism, wherein:

the mounting plate comprises a front surface and a back surface wherein the front surface is opposite the back surface;

the collar is coupled to the front surface of the mounting plate and comprises a bowl aperture;

the capture plate is coupled to the collar and comprises a keyhole slot aperture comprising a wide end and a narrow end, the keyhole slot aperture is aligned with the bowl aperture longitudinally such that the narrow end partially covers the bowl aperture;

the wedge release is coupled to the collar;

the wedge bias spring is coupled between the collar and the wedge release to bias the wedge release in a locked position;

the at least one mounting stud is coupled to the back surface of the mounting plate, each of the at least one mounting stud comprising a stem portion that extends outwardly from the back surface of the mounting plate and an enlarged head portion disposed at a distal end of the stem portion; and the release mechanism is coupled to the mounting plate and comprises:

a locking pin disposed through the mounting plate and extending outwardly from the back surface in an extended position, a spring which biases the locking pin in the extended position, and at least one locking in release operatively coupled to the locking in to transition the locking pin between a retracted position and the extended position;

wherein the equipment mount comprises a wedge interface comprising an equipment plate, a bowl, and a wedge wherein:

the bowl comprises a plurality of capture guides on opposite sides of the bowl; and the wedge is coupled between the equipment plate and the bowl and comprises a lead-in surface and two inclined surfaces to aid in an alignment of the wedge with the narrow end of the keyhole slot aperture when the wedge slidably couples with the keyhole slot aperture of the capture plate.

2. The equipment mount as claimed in claim 1 wherein the bowl comprises a capture trough and the wedge release comprises a blade wherein:

the blade is flush with a bottom surface of the bowl aperture when the wedge release is in an unlocked position, and the blade is not flush with the bottom surface of the bowl aperture when the wedge release is in the locked position and is positioned to engage the capture trough of the bowl when the bowl is inserted into the bowl aperture to restrict a movement of the wedge interface in relation to the bowl aperture.

3. The equipment mount as claimed in claim 1 wherein the bowl aperture comprises a plurality of guide walls and the bowl comprises a plurality of sides, the plurality of guide walls guide the equipment plate into alignment with the bowl aperture when the plurality of sides makes contact with the plurality of guide walls.

4. The equipment mount as claimed in claim 1 wherein the wedge interface is configured to be coupled to a medical device.

5. The equipment mount as claimed in claim 1 wherein the lead-in surface and the two inclined surfaces center the wedge interface in the keyhole slot aperture.

* * * * *

UNITED STATES PATENT AND TRADEMARK OFFICE
CERTIFICATE OF CORRECTION

PATENT NO. : 9,611,975 B2
APPLICATION NO. : 14/766255
DATED : April 4, 2017
INVENTOR(S) : Robert Chinn et al.

It is certified that error appears in the above-identified patent and that said Letters Patent is hereby corrected as shown below:

In the Claims

Column 25, Claim 1, Lines 1-2:
"at least one locking in release operatively coupled to the locking in to transition the locking pin between a"
Should read:
--at least one locking pin release operatively coupled to the locking pin to transition the locking pin between a--.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*